United States Patent
McMahon et al.

(10) Patent No.: US 7,851,459 B2
(45) Date of Patent: Dec. 14, 2010

(54) METHODS FOR DILUTING WATER-STABILIZED ANTIMICROBIAL ORGANOSILANE COMPOSITIONS

(75) Inventors: Robert McMahon, Mableton, GA (US); William Crook, Isle of Wight (GB)

(73) Assignee: Vitec Speciality Chemicals Limited, London (GB)

( * ) Notice: Subject to any disclaimer, the term of this patent is extended or adjusted under 35 U.S.C. 154(b) by 287 days.

(21) Appl. No.: 12/203,213

(22) Filed: Sep. 3, 2008

(65) Prior Publication Data

US 2009/0069270 A1    Mar. 12, 2009

(30) Foreign Application Priority Data

Sep. 6, 2007 (EP) .................................. 07115850

(51) Int. Cl.
*A01N 55/00* (2006.01)
*A01N 25/34* (2006.01)
*A01N 25/28* (2006.01)

(52) U.S. Cl. ........................ 514/63; 424/411; 424/417; 424/421

(58) Field of Classification Search ................... 514/63; 424/411, 417, 421
See application file for complete search history.

(56) References Cited

FOREIGN PATENT DOCUMENTS

| WO | WO 99/03865 | 1/1999 |
|---|---|---|
| WO | WO 2007/099144 A | 9/2007 |

OTHER PUBLICATIONS

U.S. Appl. No. 12/203,203, filed Sep. 3, 2008, McMahon et al.

*Primary Examiner*—Raymond J Henley, III
(74) *Attorney, Agent, or Firm*—Saliwanchik, Lloyd & Saliwanchik

(57) ABSTRACT

The present invention relates to methods for diluting water-stable organosilane compositions comprising an organosilane, optionally having a non-hydrolyzable organic group, but having one or more hydrolyzable groups, and an acidified stabilizing solution prepared from at least one acid, and at least one cationic surfactant, preferably at least one quaternary ammonium salt (QAS), in water. The organosilane composition is diluted with a glycol ether. The resultant diluted organosilane composition may be used to antimicrobially treat a substrate.

39 Claims, No Drawings

METHODS FOR DILUTING WATER-STABILIZED ANTIMICROBIAL ORGANOSILANE COMPOSITIONS

FIELD OF THE INVENTION

The invention relates to methods for diluting antimicrobial organosilane compositions. In particular, this invention provides methods for diluting, with glycol ether, water-stable antimicrobial organosilane compounds stabilized with an acidified stabilized solution prepared from at least one quaternary ammonium salt.

BACKGROUND OF THE INVENTION

Organosilanes of the general formula $R_nSiX_{4-n}$ where n is an integer from 0 to 3, but more generally from 0 to 2 (where when n is 3, the organosilanes may only dimerize); R is a non-hydrolyzable organic group, such as, but not limited to, alkyl, aromatic, organofunctional, or a combination thereof, and X is alkoxy, such as methoxy or ethoxy, are prone to self-condensation rendering such organosilanes unstable in water over commercially relevant periods of time. Additionally, X can be a halogen, such as Cl, Br, or I, and is similarly liberated as HCl, HBr, or HI. For such organosilanes, the X moiety reacts with various hydroxyl containing molecules in aqueous media to liberate methanol, ethanol, HCl, HBr, HI, $H_2O$, acetic acid, or an unsubstituted or substituted carboxylic acid and to form the hydroxylated, but condensation-prone compound.

For organosilanes $R_nSiX_{4-n}$, where n is an integer from 0 to 2, hydrolysis of the first two X groups with water produces a species bearing —Si(OH)$_2$— units that can self-condense through the hydroxyl moieties to linear and/or cyclic oligomers possessing the partial structure HO—Si—(O—Si)$_{mm}$—O—Si—O—Si—O—Si—OH, where mm is an integer such that an oligomer is formed. For those cases, RSiX$_3$, hydrolysis of the third X group generates a silanetriol (RSi(OH)$_3$), which produces insoluble organosilicon polymers through linear and/or cyclic self-condensation of the Si(OH) units. This water induced self-condensation generally precludes storage of most organosilanes $R_nSiX_{4-n}$, where n ranges from 0 to 2, inclusive, in water. Except for some organosilanes that are stable in very dilute solutions at specific pH ranges, the use of water solutions of most organosilanes require the use of freshly prepared solutions.

One commercially relevant example of an organosilane suffering from such undesirable self-condensation is the antimicrobial Dow Corning 5700 (Dow Corning Corporation, Midland, Mich.). The literature describes the active ingredient of Dow Corning 5700 as 3-(trimethoxysilyl)propyl-dimethyloctadecyl ammonium chloride. However, in aqueous media, it is believed that the correct active ingredient is more likely 3-(trihydroxysilyl)propyl-dimethyloctadecyl ammonium chloride. Nonetheless, Dow Corning 5700 is a water activated antimicrobial integrated system that is capable of binding to a wide variety of natural and synthetic substrates, including fibers and fabrics, to produce a durable surface or fabric coating. 3-(Trimethoxysilyl)propyl-dimethyloctadecyl ammonium chloride is prepared by quaternization of dimethyloctadecylamine with 3-chloropropyl trimethoxysilane.

The $C_{18}$ hydrocarbon chain quaternary ammonium portion of the molecule possesses long-acting antimicrobial properties and provides initial association with the surface of the substrate through ionic bonds and/or electrostatic interaction. Preferably, the treated surface becomes permanently coated with a covalently bound octadecylammonium ion providing a durable, long-acting antimicrobial coating that is able to destroy microbes that come into contact with the surface.

Unfortunately, as noted above, organosilanes in water, such as the activated mixture of 3-(trimethoxysilyl)propyl-dimethyloctadecyl ammonium chloride and water, are generally unstable and prone to self-condensation. For instance, the mixture of 3-(trimethoxysilyl)propyl-dimethyloctadecyl ammonium chloride and water begins to lose effectiveness in as little as four to eight hours. Gel formation in this and similar silane formulations in water begins to occur in even shorter times. The limitations of such organosilanes in aqueous media are further described in U.S. Pat. No. 5,411,585, the contents of which are hereby incorporated by this reference. Moreover, such products are notorious for agitation difficulty during the addition of the silane to water. A limited list of additives useful for stabilizing organosilanes in water are described in U.S. Pat. Nos. 5,954,069; 6,113,815; 6,469,120; and 6,762,172.

The use of quaternary ammonium silicon compounds as antimicrobial agents in accordance with the prior art is well known and taught in a wide variety of United States patents, for example, U.S. Pat. Nos. 3,560,385; 3,794,736; and 3,814,739; the contents of which are hereby incorporated by reference. It is also taught that these compounds possess certain antimicrobial properties that make them valuable and very useful for a variety of surfaces, substrates, instruments, and applications (see, for example, U.S. Pat. Nos. 3,730,701; 3,794,736; 3,860,709; 4,282,366; 4,504,541; 4,615,937; 4,692,374; 4,408,996; and 4,414,268; the contents of which are hereby incorporated by reference). While these quaternary ammonium silicon compounds have been employed to sterilize or disinfect many surfaces, their employment is still limited because of their toxicity often as a result of the solvent system used to deliver the compound, the necessity for a solvent solution (for instance, Dow Corning antimicrobial agents contain 50% methanol), short term stability (stability of aqueous silane solutions varies from hours to several weeks only), and poor water solubility. For instance, while 3-(trimethoxysilyl)propyl-dimethyloctadecyl ammonium chloride does not suffer from water insolubility, it is difficult to dissolve in water and tends to form lumps before it slowly dissolves. It is unstable in water, and, because it is shipped in 50% methanol, it is overly toxic and flammable. Many other antimicrobial organosilanes, especially quaternary ammonium silicon compounds, also suffer from problems associated with physical health hazards—precautions must be taken to avoid contact with both skin and eyes, accidental spills to the surrounding area, flammability, and the added manufacturing steps needed in order to incorporate such antimicrobial agents into other articles and surfaces, resulting in much higher manufacturing costs.

Water-stabilised organosilane compositions are described in our previous patent application, PCT/EP2007/051946, published as WO2007/099144. This discloses compositions comprising an organosilane at a variety of concentrations ranging from 0.1 wt % to 50 wt % of the composition. Water-stabilised compositions are also disclosed in WO99/03865. In this reference, the compositions are formed by mixing an organosilane with an ether. The compositions of different concentrations have different commercial applications. It would therefore be desirable to be able to dilute a concentrated organosilane composition to form a composition having the requisite concentration of organosilane for the intended use of the composition. The obvious method of dilution would be to add water to the composition. This is indeed suggested in WO2007/099144 and WO99/03865. However, the present inventors have surprisingly found that using glycol ether to dilute the composition results in a more stable composition than diluting with water and have thereby arrived at the present invention.

BRIEF SUMMARY OF THE INVENTION

In accordance with the invention, there is provided a method for reducing the concentration of organosilane in a first composition comprising an organosilane and an acidic stabilizing solution, wherein the acidic stabilizing solution comprises at least one acid, and at least one cationic surfactant in water, comprising adding glycol ether to the first composition to form a second, diluted composition. Advantageously, these compositions are not oil-in-water emulsions.

Thus, the method according to this invention allows highly concentrated, stable organosilane compositions that are essentially non-toxic to be diluted to form weaker compositions which are stable and have antimicrobial activity. The highly concentrated compositions are suitable for transporting from their place of manufacture to their site of dilution. Purchasers of the concentrated organosilane compositions may dilute the composition themselves using the method of this invention to give a variety of different diluted organosilane compositions, suitable for different purposes. Advantageously, the diluent used in this invention is glycol ether, which is relatively inexpensive and widely available.

The invention also provides a method for producing a diluted antimicrobial organosilane composition, comprising:
a) mixing at least one cationic surfactant and optionally at least one glycol ether with water to produce a solution;
b) adding at least one acid to the solution to acidify the solution;
c) adding the solution to an organosilane to form an organosilane composition; and
d) adding glycol ether to the organosilane composition to produce the diluted anti-microbial organosilane composition.

The invention also provides methods as detailed above, further comprising a step of treating a substrate with the diluted composition.

The invention also provides methods as detailed above, further comprising a step of antimicrobially enhancing a product with the diluted composition.

DETAILED DISCLOSURE OF THE INVENTION

Definitions

The present invention may be understood more readily by reference to the following detailed description of preferred embodiments of the invention.

Before the present methods are described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Throughout this application, where publications are referenced, the disclosures of these publications in their entireties are hereby incorporated by reference into this application.

The term "alkyl" as used herein refers to a branched or unbranched saturated hydrocarbon group of 1 to 24 carbon atoms, such as methyl ("Me"), ethyl ("Et"), n-propyl, isopropyl, n-butyl, isobutyl, t-butyl, octyl, decyl, tetradecyl, hexadecyl, eicosyl, tetracosyl, and the like. The term "cycloalkyl" intends a cyclic alkyl group from three to eight, preferably five or six carbon atoms. "Alkyl alcohol" refers to alkyl having attached thereto one or more hydroxy moieties, such as, but not limited to, —$CH_2CH_2OH$, $CH_2CH(OH)CH_3$, $CH_2OH$, $CH_2CH_2CH_2OH$, $CH_2CH_2CH(OH)CH_3$, $CH_2CH_2CH(OH)CH_2OH$, or $CH_2CH(OH)CH(OH)CH_3$. The term "small chain alkyl" refers to methyl, ethyl, propyl, and butyl.

The term "alkoxy" as used herein intends an alkyl group bound through a single terminal ether linkage; that is, an "alkoxy" group may be defined as —OR where R is alkyl as defined above. "Polyether" refers to a compound or moiety possessing multiple ether linkages, such as, but not limited to, polyethylene glycols or polypropylene glycols. "Polyalkylethers" refers to alkyls interconnected by or otherwise possessing multiple ether linkages.

As used herein, "optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyls and lower alkyls where there is substitution.

By the term "effective amount" of a composition as provided herein is meant a sufficient amount of the compound, product, or composition to provide the desired result. As will be pointed out below, the exact amount required will vary from substrate to substrate, depending on the particular compound, product, or composition used, its mode of administration, and the like. Thus, it is not always practical to specify an exact "effective amount," especially because a range of amounts or concentrations will usually be effective. However, an appropriate effective amount may be determined by one of ordinary skill in the art using only routine experimentation as a matter of optimization.

The term "aryl" as used herein refers to a compound or moiety whose molecules have a ring or multiple ring structure characteristic of benzene, naphthalene, phenanthrene, anthracene, etc., such as, either the six-carbon ring of benzene or the condensed six-carbon rings of the other aromatic derivatives, including, but not limited to phenyl, benzyl, naphthyl, benzylidine, xylyl, styrene, styryl, phenethyl, phenylene, benzenetriyl, etc.

As used herein, the term "aromatic" refers to the group of unsaturated cyclic hydrocarbons, typified by benzene, having a 6-carbon ring containing three double bonds or multiple attached benzene rings. Moreover, certain five membered cyclic compounds, such as furan (heterocyclic), are analogous to aromatic compounds. Aromatics include the cyclic compounds based upon a benzene functionality, as specified for "aryl" above.

Moreover, the term "cyclic" is used to refer to all aliphatic or aromatic hydrocarbons having one or more closed rings, whether unsaturated or saturated. Preferably, cyclic compounds possess rings from 5 to 7 carbon atoms, preferably 6 carbon atoms. Such rings fall into three classes: alicyclic, aromatic ("arene"), and heterocyclic. Moreover, when used with respect to cyclic compounds or moieties, the term "unsaturated" refers to such compound or moiety possessing at least one double or triple bond or otherwise constituting an aromatic compound or moiety. Moreover, the term "saturated" refers to compounds or moieties possessing no double or triple bonds, that is, where all available valence bonds of an atom, especially carbon, are attached to other atoms.

The term "heteroaryl" refers to an aryl where one or more of the carbon atoms of a ring have been substituted with a heteroatom, including, but not limited to, O, N, or S.

Similarly, the term "heterocyclic" refers to a cyclic compound or moiety where one or more of the carbon atoms of the ring have been substituted with a heteroatom, including, but not limited to O, N, or S.

As used herein, especially in reference to alkyl and alkoxy, the term "lower" refers to a moiety having from 1 to 6 carbon atoms, preferably 1 to 4 carbon atoms.

As used herein, the term "suitable" is used to refer to a moiety that is compatible with the compounds, products, or compositions as provided herein for the stated purpose. Suitability for the stated purpose may be determined by one of ordinary skill in the art using only routine experimentation.

As used herein, "substituted" is used to refer, generally, to a carbon or suitable heteroatom having a hydrogen or other atom removed and replaced with a further moiety. In one embodiment, halogen, hydroxy, and nitrogen-based substitutions of hydrocarbon hydrogens are contemplated as within the scope of the present invention for the claimed structures. Moreover, it is intended that "substituted" refer to substitutions which do not change the basic and novel utility of the underlying compounds, products, or compositions of the present invention.

"Unsubstituted" refers to a structure wherein the reference atom does not have any further moieties attached thereto or substituted therefor.

As used herein, "branched" is used to refer, generally, to a moiety having a carbon chain backbone, for example, alkyl or alkoxy, wherein the backbone may contain one or more subordinate carbon chain branches. For example, isobutyl, t-butyl, isopropyl, $CH_2CH_2C(CH_3)(H)CH_2CH_3$, $CH_2C(CH_2CH_3)(H)CH_2CH_3$, $CH_2CH_2C(CH_3)CH_3$, and $CH_2CH_2C(CH_3)_3$ would all be considered branched moieties. Moreover, it is intended that "branched" variations of the moieties herein described refer to variations that do not change the basic and novel utility of the underlying compounds, products, or compositions of the present invention. "Unbranched" refers to a structure wherein the carbon chain does not have any branches thereon, that is, where the carbon chain extends in a direct line.

As used herein, the term "acyl" refers to organic acid derived moieties of the formula RCOX where R is an organic molecule and X, instead of being hydroxy, is replaced with another substituent, preferably a suitable anion, such as a halogen including, but not limited to, F, Cl, Br, or I.

As used herein, the term "perfluoro" or "perfluoro-analog" refers to a hydrocarbon where the hydrogen atoms attached to carbons have been replaced with F atoms. Preferably, but not necessarily, in perfluoro-analogs, most, if not all, of the H atoms are replaced with F atoms. A "fluoro-" analog is contemplated to indicate a hydrocarbon where at least one hydrogen atom attached to a carbon is replaced with an F atom.

As used herein, "substrate" refers to any article, product, or surface that can be treated with the diluted organosilane compositions. Suitable substrates are generally characterized by either having a negatively charged surface of oxygen atoms, or any surface capable of electrostatically, ionically, or covalently adhering or binding to the compositions. Preferably the adhering or binding occurs at the silicon atoms of the organosilane portion of the compositions used in this invention, but such binding is not a requirement. "Substrate" also refers to materials that are treated by incorporation of the compositions. Incorporation in this case includes the process of blending and mixing, and incorporation by becoming part of the material, for example, polymer backbone and cement.

Therefore, as used herein, the term "adhere" is meant to refer to ionic, covalent, electrostatic, or other chemical attachment of a composition to a substrate.

As used herein, the term "antimicrobially enhancing" refers to the use of the organosilane compositions, preferably those wherein the organosilane has antimicrobial activity along with other ingredients, surfactants, fillers, wetting agents, pigments, dyes, antimigrants, etc., to create a composition or solution capable of fulfilling its original purpose, based upon the other ingredients, and also of providing antimicrobial protection during the particular application.

The term "enhance" refers to the addition of antimicrobial activity to such compositions where no such activity previously existed, or to the increase of antimicrobial activity where the starting compositions or solutions already possessed antimicrobial activity.

As used herein, "hydrolyzable" refers to whether the moiety is capable of or prone to hydrolysis (for example, splitting of the molecule or moiety into two or more new molecules or moieties) in aqueous or other suitable media. Conversely, "non-hydrolyzable" refers to moieties that are not prone to or capable of hydrolysis in aqueous or other suitable media.

As used herein, "cationic" is used to refer to any compound, ion, or moiety possessing a positive charge. Moreover, "anionic" is used to refer to any compound, ion, or moiety possessing a negative charge. Furthermore, "monovalent" and "divalent" are used to refer to moieties having valances of one and two, respectively.

As used herein, the term "salt" is meant to apply in its generally defined sense as "compound formed by replacing all or part of the hydrogen ions of an acid with one or more cations of a base." See, for example, American Heritage Dictionary, Definition of "Salt" (1981). Therefore, suitable salts for the present invention may be formed by replacing a hydrogen ion of a moiety with a cation, such as $K^+$, $Na^+$, $Ca^{2+}$, $Mg^{2+}$, etc. In addition, other suitable methods of generating salts are specified throughout this specification and are within the scope of the present definition. For the purposes of the present invention, the specific identity of the cation used for forming the salt is of lesser importance than the chemical structure of the anion of which the salt is formed.

As used herein, "food article" refers to perishable or non-perishable foods such as meats, fruits and vegetables and other foods such as grains and dairy products. In preferable embodiments, the food articles referred to herein are those that are perishable or prone to spoilage upon exposure to microbes or other pathogens. In addition, a "consumable product" is meant to refer to food articles, fluids for drinking, medicines for ingestion, or any other product introduced internally via any means into a human or animal.

As used herein, the term "antimicrobial" is used in its general sense to refer to the property of the described composition, or article to prevent or reduce the growth, spread, formation, or other livelihood of organisms such as bacteria, viruses, protozoa, molds, or other organisms likely to cause spoilage or infection.

As used herein, the term "medical article" is used to refer to any suitable substrate that is or may come into contact with medical patients (human or animal), medical caregivers, bodily fluids, or any other source of contamination or infection generally associated with hospitals, clinics, physician's offices, etc.

As used herein, the terms "quaternary ammonium salt" or "quaternary ammonium salts" refer to salts of quaternary ammonium cations with an anion and are interchangeable with the acronym "QAS" or "quat".

The terms "comprising", "consisting of", and "consisting essentially of" are defined according to their standard meaning and may be substituted for one another throughout the instant application in order to attach the specific meaning associated with each term.

As used in this specification and the appended claims, the singular forms "a", "an", and "the" include plural reference unless the context clearly dictates otherwise. Thus, for example, a reference to "a composition" includes more than one such composition, a reference to "the substrate" includes more than one such substrate, and the like.

The present invention provides methods for diluting organosilane compositions. In particular, the present invention is useful in diluting a broad variety of organosilane compositions of the general formula $R_nSiX_{4-n}$ where n is an integer from 0 to 3, preferably 0 to 2; R is a non-hydrolyzable organic group, such as but not limited to, alkyl, aromatic, organofunctional, or a combination thereof; and X is halogen, such as but not limited to, Cl, Br, or I, or X is hydroxy, alkoxy such as methoxy or ethoxy, acetoxy, or unsubstituted or substituted acyl. For such organosilanes, X is prone to react with various hydroxyl containing molecules.

The solutions both concentrated and when diluted, are stable for extended periods, for example, from several days to several months. Aqueous silane stock solutions of up to 50% silane may be stabilized with the acidified stabilizing solution disclosed herein. Working silane concentrations tend to be in the 0.001-15% silane range.

The diluted solutions of the present invention are, in certain preferred embodiments, useful for the application of various organosilane coupling agents to surfaces in industrial and household uses without the use of toxic and/or flammable organic solvents. One of ordinary skill in the art would recognize that the preparation steps are merely guidelines and such a person would, without undue experimentation, be able to prepare the composition by varying the parameters for contacting or mixing the organosilane of interest and the acidified stabilizing solution and order of introduction of reagents and starting materials without deviating from the basic and novel characteristics of the present invention.

Compositions

The concentrated organosilane composition is formed from mixing an organosilane of the formula:

where n is an integer from 0 to 3, preferably 0 to 2; each R is, independently, a non-hydrolyzable organic group; and each X is, independently, a hydrolyzable group and an acidic stabilizing solution comprising at least one acid, optionally at least one glycol ether, and at least one cationic surfactant in water. Preferably, the acid is an inorganic acid. More preferably, the acid is a mineral acid. Most preferably, the acid is hydrochloric acid. Preferably, the glycol ether is diethylene glycol butyl ether (CAS # 112-34-5). Preferably, the cationic surfactant is a quaternary ammonium salt; preferably a dialkyl quat, a dialkyl/alkyl benzyl quat, or dialkyl dimethyl quat or similar quaternary surfactants, more preferably an N-alkyl-N,N-Dimethyl-N-Benzyl ammonium chloride (CAS # 68424-85-1). Preferably, the pH of the acidic stabilizing solution is between about 2 and about 3. More preferably, the pH is about 2.5.

The concentrated organosilane is stable for at least 3 days, typically for at least one week after preparation. Thus, the dilution step with glycol ether can take place at least 3 days, for instance at least one week after preparation of the concentrated organosilane composition.

Surfactants

Generally, QAS take the form of structure I:

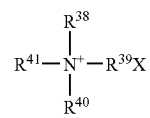

(I)

wherein each of $R^{38}$, $R^{39}$, $R^{40}$, and $R^{41}$ are independently selected from the group consisting of alkyl, aryl, and aralkyl, or the nitrogen may be part of a ring system; and X is an anion.

Preferably, at least one of $R^{38}$, $R^{39}$, $R^{40}$, or $R^{41}$ is an alkyl. More preferably, the alkyl substituent has a $C_6$ to $C_{18}$ hydrocarbon chain. Most preferably, the alkyl substituent has a $C_{12}$ to $C_{16}$ hydrocarbon chain. In yet another embodiment, at least one of $R^{38}$, $R^{39}$, $R^{40}$, or $R^{41}$ is a methyl substituent. In yet another embodiment, at least one of $R^{38}$, $R^{39}$, $R^{40}$, or $R^{41}$ is a methyl substituent, and at least one of $R^{38}$, $R^{39}$, $R^{40}$, or $R^{41}$ is an alkyl having a $C_6$ to $C_{18}$ hydrocarbon chain.

In a specific embodiment, $R^{38}=R^{39}=R^{40}=R^{41}$. In yet another embodiment, three of the four R substituents are selected from the same substituent. In yet another embodiment, two of the four R substituents are selected from the same substituent; the remainder of the substituents are either different from each other or the same as each other. In yet another embodiment, each R substituent is different.

Exemplary quaternary ammonium salts include, for example and without limitation, (1-methyldodecyl)-trimethylammonium bromide, N-alkyl($C_{12}$-$C_{16}$)—N,N-dimethyl-N-benzyl ammonium chloride, trimethyl tallow ammonium chloride, polyquaternary ammonium chloride, tetramethylammonium bromide, benzyl tributyl ammonium chloride, benzyl triethyl ammonium bromide, benzyl trimethyl ammonium chloride, cetyl pyridinium bromide, cetyl pyridinium chloride, cetyl trimethyl ammonium bromide, didecyl dimethyl ammonium chloride, dimethyl distearyl ammonium bisulfate, dimethyl distearyl ammonium methosulfate, dodecyl trimethyl ammonium bromide, dodecyl trimethyl ammonium chloride, methyl tributyl ammonium chloride, methyl tributyl ammonium hydro sulfate, methyl tricaprylyl ammonium chloride, methyl trioctyl ammonium chloride, myristyl trimethyl ammonium bromide, phenyl trimethyl ammonium chloride, tetrabutyl ammonium borohydride, tetrabutyl ammonium bromide, tetrabutyl ammonium chloride, tetrabutyl ammonium fluoride, tetrabutyl ammonium hydrogen sulfate, tetrabutyl ammonium hydroxide, tetrabutyl ammonium iodide, tetrabutyl ammonium perchlorate, tetraethyl ammonium bromide, tetraethyl ammonium chloride, tetraethyl ammonium hydroxide, tetrahexyl ammonium bromide, tetrahexyl ammonium iodide, tetramethyl ammonium bromide, tetramethyl ammonium chloride, tetramethyl ammonium fluoride, tetramethyl ammonium hydroxide, tetramethyl ammonium iodide, tetraoctyl ammonium bromide, tetrapropyl ammonium bromide, tetrapropyl ammonium chloride, tetrapropyl ammonium hydroxide, tributyl methyl ammonium chloride, triethyl benzyl ammonium chloride, N-alkyl(60% $C_{14}$, 30% $C_{16}$, 5% $C_{12}$, 5% $C_{18}$) dimethyl benzyl ammonium chloride, N-alkyl(68% $C_{12}$, 32% $C_{14}$) dimethyl ethylbenzyl ammonium chloride.

Acids

Preferably, the acid utilized to acidify the stabilizing solution is an inorganic acid. More preferably, the acid is a mineral acid. Most preferably, the acid is hydrochloric acid.

In another specific embodiment, the acid is an organic acid, preferably acetic acid.

However, the present invention encompasses acids including, for example and without limitation, acetic, adipic, anisic, arsenic, arsenious, benzoic, boric, bromic, bromous, butanoic, capric, caproic, caprylic, carbonic, chloric, chlorous, chromic, chromous, cinnamic, citric, cyanic, cyanoacetic, diphosphonic, disulfuric, disulfurous, dithionic, dithionous, ferricyanic, ferrocyanic, fluorosilicic, formic, fulminic, fumaric, gallic, glutaric, glycolic, hexadecanoic, hexafluorosilicic, hydrobromic, hydrochloric, hydrocyanic, hydrofluoric, hydroiodic, hydroxybenzoic, hypochlorous, iodic, iodous, isocyanic, isothiocyanic, lactic, lauric, levulinic, maleic, malic, malonic, manganic, molybdic, nitric, nitrous, octadecanoic, oleic, oxalic, pentanoic, valeric, perchloric, periodic, pertechnetic, phosphinic, phosphonic, phosphoric, phthalic, picric, propanoic, pyrogallic, pyruvic, rhenic, salicylic, selenic, selenious, silicic, stearic, succinic, sulfanilic, sulfuric, sulfurous, tartaric, telluric, tellurous, thioacetic, thiocyanic, thiosulfurous, titanic, tungstic, uranic, valeric, and vanillic acids.

Preferably, the concentration of the acid is about 1 $\underline{M}$.

Moreover, a sufficient amount of acid is added to the stabilizing solution to reduce the acidity to a pH level within the range of about 2 to about 5, more typically from about 2 to about 4 or from about 2 to about 3. In one embodiment, the pH is lowered to within the range 2.75 to 3.75. In one specific embodiment, the pH is about 2. In yet another specific embodiment, the pH is about 2.5. In yet another specific embodiment, the pH is about 3. Although previous organosilane compositions have been known to be water-stable at unknown pHs (U.S. Pat. No. 6,762,172), surprisingly, the present invention's compositions were unexpectedly found to be water-stable for at least several days when the pH was reduced to a level between about 2 and about 3. Preferably, the pH of the compositions and products of the present invention is about 2.5. There has never been a teaching about this particular pH effect on the stability of aqueous organosilane compositions.

The present invention also contemplates adding a sufficient amount of a base to adjust the pH to the desired target pH. Preferably, the base is NaOH.

Glycol Ethers

The acidic stabilizing solution may, or may not comprise glycol ether. Although previous organosilanes have been stabilized with polyols that possibly contain an ether group (U.S. Pat. Nos. 5,959,014; 6,221,944; and 6,632,805), the glycol ethers used in the present invention are not polyols. The glycol ethers utilized in the present invention do not have multiple hydroxyl moieties (that is, more than three) as suggested in the aforementioned patents nor are the hydroxyl and ether moieties required to be spaced apart by a minimum number of elements. Moreover, an acidic stabilizing solution prepared from only a glycol ether and water is unlikely to prevent self-condensation of the organosilane of interest. It is the combination of both the at least one QAS and the glycol ether in an aqueous, acidic solution that provides the requisite stability to the antimicrobial organosilane. The preferred glycol ether utilized in the present invention, in both the acidic stabilizing solution and for the dilution is diethylene glycol butyl ether. Advantageously, the addition of a glycol ether improves the wetting and dispersion properties of the present invention. The components disperse in water quickly with a minimum of physical mixing of agitation.

Exemplary glycol ethers useful in the present invention include, but are not limited to:

ethylene glycol monobutyl ether, ethylene glycol monoethyl ether, ethylene glycol monobutyl ether acetate, diethylene glycol monobutyl ether acetate, diethylene glycol monoethyl ether, propylene glycol n-butyl ether (DB), propylene glycol methyl ether (PM), propylene glycol methyl ether acetate (PMA), ethylene glycol butyl ether (EB), triethylene glycol monomethyl ether, triethylene glycol monoethyl ether, triethylene glycol monobutyl ether, ethylene glycol phenyl ether, diethylene glycol n-butyl ether acetate, diethylene glycol monobutyl ether, ethylene glycol n-butyl ether acetate, hydroxy-polyether, diethylene glycol monohexyl ether, ethylene glycol monohexyl ether, diethylene glycol monomethyl ether, ethylene glycol n-propyl ether, dipropylene glycol methyl ether, dipropylene glycol methyl ether acetate, dipropylene glycol n-butyl ether, dipropylene glycol n-propyl ether, propylene glycol n-butyl ether, propylene glycol n-propyl ether, propylene glycol phenyl ether, tripropylene glycol methyl ether, tripropylene glycol n-butyl ether, and dipropylene glycol dimethyl ether.

Additional stability may be achieved by mixing the organosilane with the acidified stabilizing solution in a non-aqueous solvent. In such an alternative preparation, the remaining solvent (for example, methanol) is liberated via distillation, freeze-drying, evaporation or other methods known in the art for removal of volatile organic solvents.

Advantageously, the diluted organosilane composition is stable following freezing and thawing. Previous organosilane compositions have polymerized during and immediately after thawing from a frozen state. Surprisingly, the present invention is able to withstand multiple cycles of freezing and thawing without destabilizing by polymerization. Without being limited by theory, it is believed that the acidic stabilizing solution protects the silane moieties of the organosilane ingredient from being punctured by water crystals that may form during freezing. The advantageous ability of the present invention to undergo freeze and thaw cycles without polymerization is particularly desirable when the invention is transported or stored in cold environments.

Organosilanes

The organosilanes may have the general formula:

$$R_nSiX_{4-n}$$

where n is an integer from 0 to 3, preferably 0 to 2;

R is a non-hydrolyzable organic group (alkyl, aromatic, organofunctional or a combination thereof); and X is hydroxy, alkoxy, preferably methoxy or ethoxy, halogen (preferably Cl, Br, or I), acetoxy, acyl, substituted acyl, or a hydrolyzable polymer or other moiety prone to hydrolysis and/or environmental harmfulness.

The organosilanes used in the practice of the present invention need not be, and often are not, water soluble. By varying the stabilizer and preparation method, the organosilanes selected for use in the present invention are solubilized in water by the stabilizer.

More preferably, in the composition prepared from mixing an organosilane of the formula:

$$R_nSiX_{4-n}$$

with the aforementioned acidic stabilizing solution, n is an integer from 0 to 2, preferably 1; each R is, independently, alkyl, preferably from 1 to 22 carbon atoms branched or unbranched, substituted or unsubstituted, more preferably from 1 to 6 carbon atoms, or from 10 to 20 carbon atoms, most preferably from 1 to 4 carbon atoms or from 14 to 18 carbon atoms; alkyl alcohol of similar carbon lengths, branching, and substitution, or aromatic, such as benzyl, phenyl, etc.; each X is, independently, hydroxy, alkoxy, halogen (such as, but not limited to, Cl, Br, I, or F), acetyl, acetoxy, acyl, a hydroxylated solid or liquid polymeric moiety, polyether or polyalkylether.

R may be substituted with $C_{1-24}$ alkyl, $C_{1-24}$ carbonic acid, R" ring substituted phenol, R" ring substituted heteroaryl, phenol, $(R'')_x$ ring substituted saturated or unsaturated cyclic alcohol, wherein x is an integer from 0 to 15. The cycle or ring size is from 3 to 8 carbon atoms and carbon atoms may be replaced with O, N and S. R" is H. F, Cl, Br, I, CN, SCN, $NH_2$, $C_{1-24}$ alkyl, acetyl, acetoxy, acyl or $X_2PO_4$, wherein X is any suitable cation. In addition R can contain up to 4 phosphate groups.

In a further embodiment of the invention, the organosilane is of the formula I, II, III, or IV $$(R^1)_3SiR^2N^+(R^3)(R^4)(R^5)Y^+ \quad (I)$$

$$(R^1)_3SiR^2N(R^3)(R^4) \quad (II)$$

$$(R^1)_3SiR^2R^{35} \quad (III)$$

$$(R^1)_2Si(R^{36})(R^{37}) \quad (IV)$$

wherein each $R^1$ is, independently, halogen or $R^6O$;

where $R^6$ is H, alkyl from 1 to about 24 carbon atoms, acetyl, acetoxy, acyl, propylene glycol, ethylene glycol, polyethylene glycol, polypropylene glycol; block and copolymers of ethylene and propylene glycol, the alkyl monoether from 1 to 24 carbons of propylene glycol, ethylene glycol, polyethylene glycol, polypropylene glycol; block and copolymers of ethylene and propylene glycol or the monoester of a carbonic acid from 1 to 24 carbons and propylene glycol, ethylene glycol, polyethylene glycol, polypropylene glycol; block and copolymers of ethylene and propylene glycol; octylphenol, nonylphenol, and sorbitan ethers;

$R^{35}$ is $R^6$, H, halogen (such as Cl, Br, F, or 1), $NH_2(CH_2)_2NHR^2NH_2R^2$, $C_3H_5O_2R^2$, $C_4H_5O_2R^2$, $NaO(CH_3O)P(O)R^2$, or $ClCH_2C_6H_4R^2$;

$R^{36}$ and $R^{37}$ are, independently, $R^{35}$, halogen, H, alkyl, preferably from 1 to 4 carbon atoms, more preferably from 1 to 2 carbon atoms, isobutyl, phenyl, or n-octyl;

$R^2$ is a divalent radical derived from benzyl, vinyl, alkyl from 1 to about 24 carbon atoms, acetyl, acetoxy, acyl, propylene glycol, ethylene glycol, polyethylene glycol, polypropylene glycol; block and copolymers of ethylene and propylene glycol, the alkyl monoether from 1 to 24 carbons of propylene glycol, ethylene glycol, polyethylene glycol, polypropylene glycol; block and copolymers of ethylene and propylene glycol or the monoester of a carbonic acid from 1 to 24 carbons and propylene glycol, ethylene glycol, polyethylene glycol, polypropylene glycol; block and copolymers of ethylene and propylene glycol; octylphenol, nonylphenol, or sorbitan ethers;

$R^3$ and $R^4$ are, independently, $R^{35}$, alkyl alcohol or alkoxy, preferably 1 to about 10 carbon atoms, more preferably alkyl from 1 to 4 carbon atoms, or more preferably from 1 to 2 carbon atoms;

$R^3$ and $R^4$ can, together, form a morpholine or cyclic or heterocyclic, unsaturated or saturated, five to seven-membered ring of the formula V:

$$-R^3-(R^7)_k-R^4- \quad (V)$$

where k is an integer from 0 to 2, preferably 0 to 1, most preferably 1;

$R^7$, where the ring is saturated is $CH_2$, O, S, NH, $NH_2^+$, $NCH_2CH_2NH_2$, $NCH_2CH_2NH_3^+$, $NCH_2CH_2N(R^8)(R^9)$, $NCH_2CH_2N^+(R^8)(R^9)(R^{10})$, N(alkyl), N(aryl), N(benzyl), where each $R^8$, $R^9$, and $R^{10}$ is, independently, benzyl, $R^{37}$, polyether, preferably from 1 to 4 carbon atoms, alkyl alcohol, preferably from 1 to 4 carbon atoms, alkoxy, preferably from 1 to 4 carbon atoms, or alkyl, from 1 to 24 carbon atoms, preferably 1 to about 10 carbon atoms, and the "alkyl" specified above is from 1 to 24 carbon atoms, more preferably from 1 to 10 carbon atoms, most preferably from 1 to 3 carbon atoms, the "aryl" is more preferably phenyl or benzyl, and $R^7$, where the ring is unsaturated is CH, N, $N^+H$, $N^+(alkyl)$, $N^+(aryl)$, $N^+(benzyl)$, $N-CH_2-N$, $N^+H-CH_2-N$, $N^+(alkyl)-CH_2-N$, $N^+(aryl)-CH_2-N$, or $N^+(benzyl)-CH_2-N$, where the alkyl, aryl, or benzyl is as described above; wherein the ring is unsubstituted or substituted with alkyl from 1 to 24 carbon atoms, more preferably from 1 to 10 carbon atoms, most preferably from 1 to 3 carbon atoms, ester, aldehyde, carboxylate (preferably acetoxy, acetyl, acyl or perfluorocarboxylate) amide, thionamide, nitro, amine, or halide, most preferably Cl, Br, or I;

and the ring provided by formula V represents $R^3$ or $R^4$, independently, with the ring nitrogen of formula I or II replaced by CH or $CH_2$. This ring is attached to the nitrogen in structure I or II, by removing any one hydrogen from the structure and placing a bond from the nitrogen of I or II to the atom missing the hydrogen.

$R^5$ is alkyl alcohol, preferably from 1 to 6 carbon atoms, more preferably from 1 to 4 carbon atoms, $R^{35}$, $CH_2C_6H_5$, polyether, such as a polyethylene glycol or a polypropylene glycol, alkyl from 1 to 24 carbon atoms, preferably from 1 to 10 carbon atoms, most preferably from 1 to 6 carbon atoms, alkoxy, from 1 to 24 carbon atoms, more preferably from 1 to 10 carbon atoms, most preferably from 1 to 6 carbon atoms, perfluoroalkyl, from 1 to 24 carbon atoms, more preferably from 1 to 10 carbon atoms, most preferably from 1 to 6 carbon atoms, perfluoroalkylsulfonate, from 1 to 24 carbon atoms, more preferably from 1 to 10 carbon atoms, most preferably from 1 to 6 carbon atoms, perfluoroalkylcarboxylate, or is a five to seven-membered ring of formula V as described above; and $Y^-$ is a suitable anionic moiety to form the salt of the compound of formula I, II, III, or IV. For instance, $Y^-$ may be $Cl^-$.

Preferably, $R^1$ is $R^6O$, wherein $R^6$ is preferably $C_{1-24}$ alkyl, more preferably $C_{1-6}$ alkyl. For instance, $R^1$ may be methoxy.

In another embodiment, $R^1$ is alkylene, for instance ethylene or propylene. Preferably, at least one of $R^3$ and $R^4$ is H or $C_{1-24}$ alkyl. Alternatively, $R^3$ and $R^4$ together form a benzyl ring, which may be substituted or unsubstituted.

Numerous art-known organosilanes are suitable for use in the present invention. U.S. Pat. Nos. 5,411,585; 5,064,613; 5,145,592, and the publication entitled "A Guide to DC Silane Coupling Agent" (Dow Corning, 1990) disclose many suitable organosilanes. The contents of these references are hereby incorporated in their entirety herein by this reference for the teachings of suitable organosilanes. These organosilanes are suitable for the formation of the water-stabilized organosilane compositions of the present invention. In addition, the disclosure of U.S. Pat. No. 4,390,712 is hereby incorporated by reference for its teaching of siloxane synthesis in an aqueous medium. Per the instant disclosure, those skilled in the art will appreciate that the aqueous siloxane synthesis methods of the U.S. Pat. No. 4,390,712 are modified to advantage by performing the siloxane synthesis in the presence of the QAS stabilizer as defined herein, thereby forming a stabilized siloxane-water composition while still taking advantage of the accelerated kinetics of siloxane formation in aqueous media noted in the U.S. Pat. No. 4,390,712. Accordingly, an organosilane of the formula $R_nSiX_{4-n}$ where n is an integer from 0 to 3, preferably 0 to 2; each R is, independently, a non-hydrolyzable organic group; and each X is, independently, a hydrolyzable group; may be made from starting materials in an aqueous solution in the presence of an effective amount of at least one QAS, sufficient to stabilize the organosilane as it is formed from the reactants.

Preferred silanes for use in the compositions and methods of the present invention include silanes of the following formula:

$$(R^1)_3SiR^2N^+(R^3)(R^4)(R^5)Y^- \text{ or } (R^1)_3SiR^2N^+C_5H_5Y^-$$

wherein each $R^1$ is, independently, halogen (Cl, Br, I, F) or $R^6O$, where $R^6$ is H, alkyl from 1 to about 6 carbon atoms, unsubstituted or substituted, preferably from 1 to about 2 carbon atoms and more preferably 1 carbon atom, or acetyl or other acyl, including substituted acyl; or $R^6O$ can be derived from any hydroxylated polymer, hydroxylated liquid, or hydroxylated solid regardless of water solubility; or $R^6O$ can be derived from any polyether such as, but not limited to, polyethyleneglycols or polypropyleneglycols, such as poly(propyleneglycol)triol (glycerol propoxylate);

$R^2$ is a divalent radical derived from unsubstituted or substituted benzyl or an unsubstituted or substituted alkyl from 1 to about 3 carbon atoms, preferably alkyl from 1 to 3 carbon atoms;

$R^3$ and $R^4$ are, independently, lower alkoxy from 1 to 4 carbon atoms, preferably of 2 carbon atoms, such as $CH_2CH_2OH$, $CH_2CH(OH)CH_3$, alkyl from 1 to about 22 carbon atoms, preferably from 1 to about 10 carbon atoms and most preferably from 1 to 2 carbon atoms or $R^3$ and $R^4$ can, together, form a morpholine or other cyclic or heterocyclic, unsaturated or saturated, five to seven-membered ring of the formula:

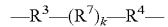

where k is an integer from 0 to 2, and $R^7$, where the ring is saturated, is $CH_2$, O, S, NH, $NH_2^+$, $NCH_2CH_2NH_2$, $NCH_2CH_2NH_3^+$, $NCH_2CH_2N(R^8)(R^9)$, $NCH_2CH_2N^+(R^8)(R^9)(R^{10})$, N(alkyl), N(aryl), N(benzyl), or $R^7$, where the ring is unsaturated is, N, $N^+H$, $N^+$(alkyl), $N^+$(aryl), $N^+$(benzyl), N—$CH_2$—N, $N^+H$—$CH_2$—N, $N^+$(alkyl)-$CH_2$—N, $N^+$(aryl)-$CH_2$—N, or $N^+$(benzyl)-$CH_2$—N;

where $R^8$, $R^9$, and $R^{10}$ are, independently, benzyl, polyether, lower alkyl alcohol from 1 to 4 carbon atoms, lower alkoxy from 1 to 4 carbon atoms, or alkyl from 1 to about 22 carbon atoms, preferably 1 to about 10 carbon atoms;

$R^5$ is $CH_2C_6H_5$, $CH_2CH_2OH$, $CH_2CH(OH)CH_3$, a polyether such as polyethyleneglycol: —$(CH_2CH_2O)_aH$, polypropyleneglycol: —$(CH_2CH(CH_3)O)_aH$, or alkylated polyoxyethylene: —$(CH_2CH_2O)_aB$ where B is alkyl from 1 to 22 carbon atoms, unsubstituted or substituted, and where each a is, independently, an integer from 1 to 12, more preferably from about 1 to about 5, or $R^5$ is alkyl or perfluoroalkyl from 1 to about 22 carbon atoms, preferably from about 12 to about 20 carbon atoms and even more preferably from 14 to about 18 carbon atoms; and Y is halogen (such as Cl, Br, I), acetate, sulfate, tosylate or carboxylate, such as acetate, polycarboxylate salts, alcoholates, functionalized carboxylate, such as trifluoroacetate and perfluoroalkylcarboxylates, or other alkyl and arylsulfonate salts, including trifluoromethylsulfonate and anionic metal oxides, perfluoroalkylsulfonate salts, phosphate and phosphonate salts, borate and boronate salts, benzoates or any other suitable anionic moiety, and the ring provided for formula V represents $R^3$ or $R^4$, independently, with the ring nitrogen of formula I or II replaced by CH or $CH_2$. This ring is attached to the nitrogen in structure I or II, by removing any one hydrogen from the structure and placing a bond from the nitrogen of I or II to the atom missing the hydrogen.

Preferred organosilanes include, but are not limited to:

3-(trimethoxysilyl)propyldimethyloctadecyl ammonium chloride, 3-(trimethoxysilyl)propylmethyldi(decyl) ammonium chloride, 3-chloropropyltrimethylsilane, octadecyltrimethoxysilane, perfluorooctyltriethoxysilane, $(CH_3O)_3Si(CH_2)_3N^+(CH_3)_2C_{18}H_{37}Cl^-$, $(CH_3O)_3Si(CH_2)_3N^+(CH_3)_2C_{18}H_{37}Br^-$, $(CH_3O)_3Si(CH_2)_3N^+(C_{10}H_{21})CH_3Cl^-$, $(CH_3O)_3Si(CH_2)_3N^+(C_{10}H_{21})CH_3Br^-$, $(CH_3O)_3Si(CH_2)_3N^+(CH_3)_3Cl^-$, $(CH_3O)_3Si(CH_2)_3N^+(CH_3)_2C_8H_{17}Cl^-$, $(CH_3O)_3Si(CH_2)_3N^+(CH_3)_2C_{10}H_{21}Cl^-$, $(CH_3O)_3Si(CH_2)_3N^+(CH_3)_2C_{12}H_{25}Cl^-$, $(CH_3O)_3Si(CH_2)_3N^+(CH_3)_2C_{14}H_{29}Cl^-$, $(CH_3O)_3Si(CH_2)_3N^+(CH_3)_2C_{16}H_{33}Cl^-$, $(CH_3O)_3Si(CH_2)_3N^+(CH_3)_2C_{20}H_{41}Cl^-$, $(CH_3O)_3Si(CH_2)_3N^+(C_4H_9)_3Cl^-$, $(CH_3O)_3Si(CH_2)_3N^+(C_2H_5)_3Cl^-$, $(CH_3CH_2O)_3Si(CH_2)_3N^+(CH_3)_2C_{18}H_{27}Cl^-$, $(CH_3O)_3Si(CH_2)_3NHC(O)(CF_2)_6CF_3$, $(CH_3O)_3Si(CH_2)_3NHC(O)(CF_2)_8CF_3$, $(CH_3O)_3Si(CH_2)_3NHC(O)(CF_2)_{10}CF_3$, $(CH_3O)_3Si(CH_2)_3NHC(O)(CF_2)_{12}CF_3$, $(CH_3O)_3Si(CH_2)_3NHC(O)(CF_2)_{14}CF_3$, $(CH_3O)_3Si(CH_2)_3NHC(O)(CF_2)_{16}CF_3$, $(CH_3O)_3Si(CH_2)_3NHSO_2(CF_2)_7CF_3$, $(CH_3O)_3Si(CH_2)_3N^+(CH_3)_2(CH_2)_3NHC(O)(CH_2)_6CH_3$, $(CH_3O)_3Si(CH_2)_3N^+(CH_3)_2(CH_2)_3NHC(O)(CH_2)_8CH_3$, $(CH_3O)_3Si(CH_2)_3N^+(CH_3)_2(CH_2)_3NHC(O)(CH_2)_{10}CH_3$, $(CH_3O)_3Si(CH_2)_3N^+(CH_3)_2(CH_2)_3NHC(O)(CH_2)_{12}CH_3$, $(CH_3O)_3Si(CH_2)_3N^+(CH_3)_2(CH_2)_3NHC(O)(CH_2)_{14}CH_3$, $(CH_3O)_3Si(CH_2)_3N^+(CH_3)_2(CH_2)_3NHC(O)(CH_2)_{16}CH_3$, $(CH_3O)_3Si(CH_2)_3N^+(CH_3)_2(CH_2)_3NHC(O)(CF_2)_6CF_3$, $(CH_3O)_3Si(CH_2)_3N^+(CH_3)_2(CH_2)_3NHC(O)(CF_2)_8CF_3$, $(CH_3O)_3Si(CH_2)_3N^+(CH_3)_2(CH_2)_3NHC(O)(CF_2)_{10}CF_3$, $(CH_3O)_3Si(CH_2)_3N^+(CH_3)_2(CH_2)_3NHC(O)(CF_2)_{12}CF_3$, $(CH_3O)_3Si(CH_2)_3N^+(CH_3)_2(CH_2)_3NHC(O)(CF_2)_{14}CF_3$, $(CH_3O)_3Si(CH_2)_3N^+(CH_3)_2(CH_2)_3NHC(O)(CF_2)_{16}CF_3$, $(CH_3O)_3Si(CH_2)_3N^+(CH_3)_2(CH_2)_3NHSO_2(CF_2)_7CF_3$, $(CH_3O)_3Si(CH_2)_3N^+(CH_3)_2(CH_2)_3NHSO_2(CF_2)_9CF_3$, $(CH_3O)_3Si(CH_2)_3N^+(CH_3)_2(CH_2)_3NHSO_2(CF_2)_{11}CF_3$, $(CH_3O)_3Si(CH_2)_3N^+(CH_3)_2(CH_2)_3NHSO_2(CF_2)_{13}CF_3$, $(CH_3O)_3Si(CH_2)_3N^+(CH_3)_2(CH_2)_3NHSO_2(CF_2)_{15}CF_3$, $(CH_3O)_3Si(CH_2)_3N^+(CH_3)_2(CH_2)_3NHSO_2(CF_2)_{16}CF_3$, aminoethylaminopropyltrimethoxysilane: $NH_2(CH_2)_2NH(CH_2)_3Si(OCH_3)_3$, 3-aminopropyltrimethoxysilane: $NH_2(CH_2)_3Si(OCH_3)_3$, 3-aminopropyltriethoxysilane: $NH_2(CH_2)_3Si(OCH_2CH_3)_3$, 3-chloropropyltrimethoxysilane: $Cl(CH_2)_3Si(OCH_3)_3$, 3-chloropropyltriethoxysilane: $Cl(CH_2)_3Si(OCH_2CH_3)_3$, 3-chloropropyltrichlorosilane: $Cl(CH_2)_3SiCl_3$, 3-glycidoxypropyltrimethoxysilane: $C_3H_5O_2(CH_2)_3Si(OCH_3)_3$, 3-glycidoxypropyltriethoxysilane: $C_3H_5O_2(CH_2)_3Si(OCH_2CH_3)_3$, 3-methacryloxypropyltrimethoxysilane: $C_4H_5O_2(CH_2)_3Si(OCH_3)_3$, 3-methacryloxypropyltriethoxysilane: $C_4H_5O_2(CH_2)_3Si(OCH_2CH_3)_3$, methyldichlorosilane: $CH_3SiHCl_2$, silane-modified melamine: Dow Corning Q1-6106, sodium (trihydroxysilyl)propylmethylphosphonate: $NaO(CH_3O)P(O)(CH_2)_3Si(OH)_3$, trichlorosilane, $SiHCl_3$, n-2-vinylbenzylamino-ethyl-3-aminopropyltrimethoxysilane HCL: Dow Corning Z-6032, vinyltriacetoxysilane: $H_2C=CHSi(OCOCH_3)_3$, vinyltrimethoxysilane: $H_2C=CHSi(OCH_3)_3$, vinyltriethoxysilane: $H_2C=CHSi(OCH_2CH_3)_3$, vinyltrichlorosilane: $H_2C=CHSiCl_3$, dimethyldichlorosilane: $(CH_3)_2SiCl_2$, dimethyldimethoxysilane: $(CH_3)_2Si(OCH_3)_2$, diphenyldichlorosilane: $(C_6H_5)_2SiCl_2$, ethyltrichlorosilane: $(C_2H_5)SiCl_3$, ethyltrimethoxysilane: $(C_2H_5)Si(OCH_3)_3$, ethyltriethoxysilane: $(C_2H_5)Si(OCH_2CH_3)_3$, isobutyltrimethoxysilane, n-octyltriethoxysilane, methylphenyldichlorosilane: $CH_3(C_6H_5)SiCl_2$, methyltrichlorosilane: $CH_3SiCl_3$, methyltrimethoxysilane: $CH_3Si(OCH_3)_3$, phenyltrichlorosilane: $C_6H_5SiCl_3$, phenyltrimethoxysilane: $C_6H_5Si(OCH_3)_3$, n-propyltrichlorosilane: $C_3H_7SiCl_3$, n-propyltrimethoxysilane: $C_3H_7Si(OCH_3)_3$, silicon tetrachloride: $SiCl_4$, $ClCH_2C_6H_4CH_2CH_2SiCl_{3n}$, $ClCH_2C_6H_4CH_2CH_2Si(OCH_3)_3$, $ClCH_2C_6H_4CH_2CH_2Si(OCH_2CH_3)_3$, decyltrichlorosilane, dichloromethyl(4-methylphenethyl)silane, diethoxymethylphenylsilane,

[3-(diethylamino)propyl]trimethoxysilane, 3-(dimethoxymethylsilyl)-1-propanethiol, dimethoxymethylvinylsilane, 3-[tris(trimethylsilyloxy)silyl]propyl methacrylate, trichloro[4-(chloromethyl)phenyl]silane, methylbis(trimethylsilyloxy)vinylsilane, methyltripropoxysilane, and trichlorocyclopentylsi lane.

The diluted organosilane composition may be used as a UV protectant, for example, in a suntan lotion, where para-amino benzoic acid, cinnamic acid, benzoic acid and benzophenone are active ingredients. These compounds and their alkyl derivatives may be attached to a silane in this invention. Attachment of the aforementioned molecules is by removal of one atom or group from these compounds and utilizing this free valence for bond formation to a silane from which an atom or group has been removed also. Additional examples are:

(CH₃O)₃Si(CH₂)₃NHC₆H₄COOH,
(CH₃O)₃Si(CH₂)₃NHC₆H₄COOCH₃,
(CH₃O)₃Si(CH₂)₃NHC₆H₄COOC₂H₅,
(CH₃O)₃Si(CH₂)₃NHC₆H₄COOC₃H₇,
(CH₃O)₃Si(CH₂)₃NHC₆H₄COOC₄H₉,
(CH₃O)₃Si(CH₂)₃NHC₆H₄COOCH₂C₆H₅,
(CH₃O)₃Si(CH₂)₃NHC₆H₄COOCH₂C₆H₄NH₂,
(CH₃O)₃Si(CH₂)₃NHC₆H₄COOCH₂C₆H₄N(CH₃)₂,
(CH₃O)₃Si(CH₂)₃NHC₆H₄COOCH₂C₆H₄N(CH₂CH₃)₂,
(CH₃O)₃Si(CH₂)₃NHC₆H₄COOCH₂C₆H₄N⁺(CH₃)₃Y⁻,
(CH₃O)₃Si(CH₂)₃NHC₆H₄COOCH₂C₆H₄N⁺(CH₂CH₃)₃Y⁻,
(CH₃O)₃Si(CH₂)₃NCH₃C₆H₄COOH,
(CH₃O)₃Si(CH₂)₃NCH₃C₆H₄COOCH₃,
(CH₃O)₃Si(CH₂)₃NCH₃C₆H₄COOC₂H₅,
(CH₃O)₃Si(CH₂)₃NCH₃C₆H₄COOC₃H₇,
(CH₃O)₃Si(CH₂)₃NCH₃C₆H₄COOC₄H₉,
(CH₃O)₃Si(CH₂)₃NCH₃C₆H₄COOCH₂C₆H₅,
(CH₃O)₃Si(CH₂)₃NCH₃C₆H₄COOCH₂C₆H₄NH₂,
(CH₃O)₃Si(CH₂)₃NCH₃C₆H₄COOCH₂C₆H₄N(CH₃)₂,
(CH₃O)₃Si(CH₂)₃NCH₃C₆H₄COOCH₂C₆H₄N(CH₂CH₃)₂,
(CH₃O)₃Si(CH₂)₃NCH₃C₆H₄COOCH₂C₆H₄N⁺(CH₃)₃Y⁻,
(CH₃O)₃Si(CH₂)₃NCH₃C₆H₄COOCH₂C₆H₄N⁺(CH₂CH₃)₃Y⁻,
(CH₃O)₃Si(CH₂)₃N⁺(CH₃)₂C₆H₄COOHY⁻,
(CH₃O)₃Si(CH₂)₃N⁺(CH₃)₂C₆H₄COOCH₃Y⁻,
(CH₃O)₃Si(CH₂)₃N⁺(CH₃)₂C₆H₄COOC₂H₅Y⁻,
(CH₃O)₃Si(CH₂)₃N⁺(CH₃)₂C₆H₄COOC₃H₇Y⁻,
(CH₃O)₃Si(CH₂)₃N⁺(CH₃)₂C₆H₄COOC₄H₉Y⁻,
(CH₃O)₃Si(CH₂)₃N⁺(CH₃)₂C₆H₄COOCH₂C₆H₅Y⁻,
(CH₃O)₃Si(CH₂)₃N⁺(CH₃)₂C₆H₄COOCH₂C₆H₄NH₂Y⁻,
(CH₃O)₃Si(CH₂)₃N⁺(CH₃)₂C₆H₄COOCH₂C₆H₄N(CH₃)₂Y⁻,
(CH₃O)₃Si(CH₂)₃N⁺(CH₃)₂C₆H₄COOCH₂C₆H₄N(CH₂CH₃)₂Y⁻,
(CH₃O)₃Si(CH₂)₃N⁺(CH₃)₂C₆H₄COOCH₂C₆H₄N⁺(CH₃)₃Y⁻,
(CH₃O)₃Si(CH₂)₃N⁺(CH₃)₂C₆H₄COOCH₂C₆H₄N⁺(CH₂CH₃)₃Y⁻,
(CH₃O)₃Si(CH₂)₃NC₂H₅C₆H₄COOH,
(CH₃O)₃Si(CH₂)₃NC₂H₅C₆H₄COOCH₃,
(CH₃O)₃Si(CH₂)₃NC₂H₅C₆H₄COOC₄H₉,
(CH₃O)₃Si(CH₂)₃NC₂H₅C₆H₄COOC₃H₇,
(CH₃O)₃Si(CH₂)₃NC₂H₅C₆H₄COOC₄H₉,
(CH₃O)₃Si(CH₂)₃NC₂H₅C₆H₄COOCH₂C₆H₅,
(CH₃O)₃Si(CH₂)₃NC₂H₅C₆H₄COOCH₂C₆H₄NH₂,
(CH₃O)₃Si(CH₂)₃NC₂H₅C₆H₄COOCH₂C₆H₄N(CH₃)₂, (CH₃O)₃Si(CH₂)₃NC₂H₅C₆H₄COOCH₂C₆H₄N(CH₂CH₃)₂,
(CH₃O)₃Si(CH₂)₃NC₂H₅C₆H₄COOCH₂C₆H₄N⁺(CH₃)₃Y⁻,
(CH₃O)₃Si(CH₂)₃NC₂H₅C₆H₄COOCH₂C₆H₄N⁺(CH₂CH₃)₃Y⁻,
(CH₃O)₃Si(CH₂)₃N⁺(C₂H₅)₂C₆H₄COOHY⁻,
(CH₃O)₃Si(CH₂)₃N⁺(C₂H₅)₂C₆H₄COOCH₃Y⁻,
(CH₃O)₃Si(CH₂)₃N⁺(C₂H₅)₂C₆H₄COOC₂H₅Y⁻,
(CH₃O)₃Si(CH₂)₃N⁺(C₂H₅)₂C₆H₄COOC₃H₇Y⁻,
(CH₃O)₃Si(CH₂)₃N⁺(C₂H₅)₂C₆H₄COOC₄H₉,
(CH₃O)₃Si(CH₂)₃N⁺(C₂H₅)₂C₆H₄COOCH₂C₆H₅,
(CH₃O)₃Si(CH₂)₃N⁺(C₂H₅)₂C₆H₄COOCH₂C₆H₄N₂Y⁻,
(CH₃O)₃Si(CH₂)₃N⁺(C₂H₅)₂C₆H₄COOCH₂C₆H₄N(CH₃)₂,
(CH₃O)₃Si(CH₂)₃N⁺(C₂H₅)₂C₆H₄COOCH₂C₆H₄N(CH₂CH₃)₂Y⁻,
(CH₃O)₃Si(CH₂)₃N⁺(C₂H₅)₂C₆H₄COOCH₂C₆H₄N⁺(CH₃)₃Y⁻Y⁻,
(CH₃O)₃Si(CH₂)₃N⁺(C₂H₅)₂C₆H₄COOCH₂C₆H₄N⁺(CH₂CH₃)₃Y⁻Y⁻,
(CH₃CH₂O)₃Si(CH₂)₃NHC₆H₄COOH,
(CH₃CH₂O)₃Si(CH₂)₃NHC₆H₄COOCH₃,
(CH₃CH₂O)₃Si(CH₂)₃NHC₆H₄COOC₂H₅,
(CH₃CH₂O)₃Si(CH²)₃NHC₆H₄COOC₃H₇,
(CH₃CH₂O)₃Si(CH₂)₃NHC₆H₄COOC₄H₉,
(CH₃CH₂O)₃Si(CH₂)₃NHC₆H₄COOCH₂C₆H₅,
(CH₃CH₂O)₃Si(CH₂)₃NHC₆H₄COOCH₂C₆H₄NH₂,
(CH₃CH₂O)₃Si(CH₂)₃NHC₆H₄COOCH₂C₆H₄N(CH₃)₂,
(CH₃CH₂O)₃Si(CH₂)₃NHC₆H₄COOCH₂C₆H₄N(CH₂CH₃)₂,
(CH₃CH₂O)₃Si(CH₂)₃NHC₆H₄COOCH₂C₆H₄N⁺(CH₃)₃Y⁻,
(CH₃CH₂O)₃Si(CH₂)₃NHC₆H₄COOCH₂C₆H₄N⁺(CH₂CH₃)₃Y⁻,
(CH₃CH₂O)₃Si(CH₂)₃NCH₃C₆H₄COOH,
(CH₃CH₂O)₃Si(CH₂)₃NCH₃C₆H₄COOCH₃,
(CH₃CH₂O)₃Si(CH₂)₃NCH₃C₆H₄COOC₂H₅,
(CH₃CH₂O)₃Si(CH₂)₃NCH₃C₆H₄COOC₃H₇,
(CH₃CH₂O)₃Si(CH₂)₃NCH₃C₆H₄COOC₄H₉,
(CH₃CH₂O)₃Si(CH₂)₃NCH₃C₆H₄COOCH₂C₆H₅,
(CH₃CH₂O)₃Si(CH₂)₃NCH₃C₆H₄COOCH₂C₆H₄NH₂,
(CH₃CH₂O)₃Si(CH₂)₃NCH₃C₆H₄COOCH₂C₆H₄N(CH₃)₂,
(CH₃CH₂O)₃Si(CH₂)₃NCH₃C₆H₄COOCH₂C₆H₄N(CH₂CH₃)₂,
(CH₃CH₂O)₃Si(CH₂)₃NCH₃C₆H₄COOCH₂C₆H₄N⁺(CH₃)₃Y⁻,
(CH₃CH₂O)₃Si(CH₂)₃NCH₃C₆H₄COOCH₂C₆H₄N⁺(CH₂CH₃)₃Y⁻,
(CH₃CH₂O)₃Si(CH₂)₃N⁺(CH₃)₂C₆H₄COOHY⁻,
(CH₃CH₂O)₃Si(CH₂)₃N⁺(CH₃)₂C₆H₄COOCH₃Y⁻, $(CH_3CH_2O)_3Si(CH_2)_3N^+(CH_3)_2C_6H_4COOC_2H_5$, $(CH_3CH_2O)_3Si(CH_2)_3N^+(CH_3)_2C_6H_4COOC_3H_7Y^-$, $(CH_3CH_2O)_3Si(CH_2)_3N^+(CH_3)_2C_6H_4COOC_4H_9Y^-$, $(CH_3CH_2O)_3Si(CH_2)_3N^+(CH_3)_2C_6H_4COOCH_2C_6H_5Y^-$, $(CH_3CH_2O)_3Si(CH_2)_3N^+(CH_3)_2C_6H_4COOCH_2C_6H_4NH_2Y^-$, $(CH_3CH_2O)_3Si(CH_2)_3N^+(CH_3)_2C_6H_4COOCH_2C_6H_4N(CH_3)_2Y^-$, $(CH_3CH_2O)_3Si(CH_2)_3N^+(CH_3)_2C_6H_4COOCH_2C_6H_4N(CH_2CH_3)_2Y^-$, $(CH_3CH_2O)_3Si(CH_2)_3N^+(CH_3)_2C_6H_4COOCH_2C_6H_4N^+(CH_3)_3Y^-Y^-$, $(CH_3CH_2O)_3Si(CH_2)_3N^+(CH_3)_2C_6H_4COOCH_2C_6H_4N^+(CH_2CH_3)_3Y^-Y^-$, $(CH_3CH_2O)_3Si(CH_2)_3NC_2H_5C_6H_4COOH$, $(CH_3CH_2O)_3Si(CH_2)_3NC_2H_5C_6H_4COOCH_3$, $(CH_3CH_2O)_3Si(CH_2)_3NC_2H_5C_6H_4COOC_2H_5$, $(CH_3CH_2O)_3Si(CH_2)_3NC_2H_5C_6H_4COOC_3H_7$, $(CH_3CH_2O)_3Si(CH_2)_3NC_2H_5C_6H_4COOC_4H_9$, $(CH_3CH_2O)_3Si(CH_2)_3NC_2H_5C_6H_4COOCH_2C_6H_5$, $(CH_3CH_2O)_3Si(CH_2)_3NC_2H_5C_6H_4COOCH_2C_6H_4NH_2$, $(CH_3CH_2O)_3Si(CH_2)_3NC_2H_5C_6H_4COOCH_2C_6H_4N(CH_3)_2$, $(CH_3CH_2O)_3Si(CH_2)_3NC_2H_5C_6H_4COOCH_2C_6H_4N(CH_2CH_3)_2$, $(CH_3CH_2O)_3Si(CH_2)_3NC_2H_5C_6H_4COOCH_2C_6H_4N^+(CH_3)_3Y^-$, $(CH_3CH_2O)_3Si(CH_2)_3NC_2H_5C_6H_4COOCH_2C_6H_4N^+(CH_2CH_3)_3Y^-$, $(CH_3CH_2O)_3Si(CH_2)_3N^+(C_2H_5)_2C_6H_4COOH\ Y^-$, $(CH_3CH_2O)_3Si(CH_2)_3N^+(C_2H_5)_2C_6H_4COOCH_3Y^-$, $(CH_3CH_2O)_3Si(CH_2)_3N^+(C_2H_5)_2C_6H_4COOC_2H_5Y^-$, $(CH_3CH_2O)_3Si(CH_2)_3N^+(C_2H_5)_2C_6H_4COOC_3H_7Y^-$, $(CH_3CH_2O)_3Si(CH_2)_3N^+(C_2H_5)_2C_6H_4COOC_4H_9Y^-$, $(CH_3CH_2O)_3Si(CH_2)_3N^+(C_2H_5)_2C_6H_4COOCH_2C_6H_5Y^-$, $(CH_3CH_2O)_3Si(CH_2)_3N^+(C_2H_5)_2C_6H_4COOCH_2C_6H_4NH_2Y^-$, $(CH_3CH_2O)_3Si(CH_2)_3N^+(C_2H_5)_2C_6H_4COOCH_2C_6H_4N(CH_3)_2Y^-$, $(CH_3CH_2O)_3Si(CH_2)_3N^+(C_2H_5)_2C_6H_4COOCH_2C_6H_4N(CH_2CH_3)_2Y^-$, $(CH_3CH_2O)_3Si(CH_2)_3N^+(C_2H_5)_2C_6H_4COOCH_2C_6H_4N^+(CH_3)_3Y^-Y^-$, and $(CH_3CH_2O)_3Si(CH_2)_3N^+(C_2H_5)_2C_6H_4COOCH_2C_6H_4N^+(CH_2CH_3)_3Y^-Y^-$.

This invention provides a method for diluting, with glycol ether, water stable compositions comprising water and an organosilane of interest mixed with an acidic stabilizing solution. The resultant diluted composition is advantageously storable and water stable. Optionally, the water stable composition further comprises an amine oxide surfactant or a nonionic surfactant, preferably alkylphenol ethoxylate. Furthermore, the compositions provide silane coatings that are capable of migration.

The weight percentage of the antimicrobial organosilane in the diluted organosilane composition varies according to the target application. It is routine for one skilled in the art to calculate how much glycol ether is required in order to dilute the organosilane composition to the required concentration.

Generally, the concentrated organosilane composition comprises from about 5 wt % to about 50 wt % of the organosilane ("active"). Preferably, the concentrated organosilane composition comprises 15-35 wt % of the active.

By definition, the diluted organosilane composition has a lower concentration of active than the concentrated organosilane composition. Typically, the diluted organosilane composition has 0.001 to 20%, more typically 0.001 to 10% or 0.001 to 5% by weight of organosilane with respect to the composition. Diluted compositions, which are useful for application to, for example, food stuffs, contain about 0.1 wt % to about 1 wt % of the antimicrobial organosilanes. In a specific embodiment, the organosilane can comprise about 0.2 wt %, 0.3 wt %, 0.4 wt %, 0.5 wt %, 0.6 wt %, 0.7 wt %, 0.8 wt %, and 0.9 wt %. In other applications, the diluted antimicrobial organosilane comprises about 1 wt % to about 15 wt % of the composition. In a specific embodiment, the weight percentage of the organosilane of interest is within the range of about 3 wt % and 7.5 wt %. In yet another embodiment, the weight percentage is about 5 wt % to about 5.5 wt %.

In the method, typically the concentration of organosilane is reduced to 0.001-80% of its original concentration, preferably to 0.01-50% of its original concentration.

In one embodiment, QAS comprises from about 0.5 wt % to about 10 wt % of the diluted organosilane composition, more preferably from about 1 to about 10 wt % of the composition.

Typically, glycol ether comprises from about 10 to about 80 wt % of the diluted composition, more preferably from about 15 to about 60 wt %, most preferably from about 20 to about 40 wt %. In one embodiment, the glycol ether comprises from about 17 wt % to about 23 wt %.

In a preferred embodiment, the diluted antimicrobial organosilane comprises 5-15 wt % of the composition, the QAS comprises about 2 wt % of the composition, diethylene glycol butyl ether comprises about 20 wt % of the composition, and water comprises the balance of composition.

In a further embodiment, the balance of the composition is water, preferably de-ionized water.

Surprisingly, the present compositions, although not oil-in-water emulsions, remain stable and do not polymerize or precipitate for at least a week after preparation. Advantageously, when the organosilane compositions and products are prepared and stored for future usage, the non-emulsified compositions and products do not self-condense nor do solids precipitate out of solution.

Additionally, the compositions do not require a siliconate salt in order to stabilize the antimicrobial organosilane in water. (cf., U.S. Pat. No. 4,503,242). Surprisingly, as discussed in more detail above, the antimicrobial organosilane of interest remains water-stable for several days by the addition of the acidified stabilizing solution.

Methods

Methods of preparing the concentrated organosilane compositions have been previously described in PCT/EP2007/051946. The mixing sequence includes first adding at least one cationic surfactant, preferably a quaternary ammonium salt, optionally a glycol ether, and water together and acidifying the solution, preferably to a pH between about 2 and about 3. Preferably, the at least one QAS comprises about 0.1 wt % to about 5 wt % of the stabilizing solution and the glycol ether comprises about 5 wt % to about 20 wt % of the solution. The balance of the solution may be water, preferably deionized water. The order of the addition of the components to the stabilizing solution is unimportant except the acid should be added to the water. The next step is adding the acidified stabilizing solution to the antimicrobial organosilane, preferably 3-(trimethoxysilyl)propyl-dimethyloctadecyl ammonium chloride. Interestingly, adding the components of the stabilizing solution to the antimicrobial organosilane without first combining them in a solution and acidifying said solution results in a polymerized composition wherein the antimicrobial organosilane self-condenses.

The organosilane may need to be stored before use. A suitable container for the organosilane is a phenolic-lined metal container, such as a drum or a can. Typically, an opened container of the organosilane is nitrogen-capped after opening to prevent oxygen from causing the organosilane to polymerise. An organosilane nitrogen-capped in this manner may be stored for up to 12 months between a temperature of 0° C. and 30° C.

The concentrated organosilane composition is then diluted with glycol ether to give the diluted organosilane composition with the required concentration of organosilane. The dilution step typically takes place at room temperature, i.e. 20 to 25° C. The organosilane composition may be stirred during dilution. However, the amount of stirring required is generally minimal. The diluted organosilane compositions may be stored in any suitable container. Borosilicate glass test tubes with PTFE-faced rubber lined phenolic screw caps are particularly suitable, since they advantageously allow the organosilane composition to be observed.

The dilution step may take place immediately, or may take place several hours, for instance 6 to 24 hours, or several days, for instance at least 2, 3, 4, 5, or 6 days later. In some embodiments of the invention, the dilution step takes place between 1 week and 2 years after the concentrated organosilane composition is formed. Typically, the dilution step takes place no more than 4 months after the concentrated organosilane composition is formed.

The concentrated organosilane composition may need to be stored before dilution. Typically, the storage container is both air tight and opaque. The concentrated organosilane compositions may be stored air tight in an opaque container at room temperature (20 to 25° C.) in Nalgene HDPE fluorinated bottles, which have excellent barrier properties to oxygen and solvent transmission. Nalgene HDPE fluorinated caps with PTFE liners may be used to seal the bottles.

A further suitable container is made from borosilicate glass, coupled with a HDPE cap with a PTFE liner. Such a container protects the organosilane composition from light for up to 2 years at ambient temperatures between 0° C. and 30° C.

Uses

The diluted organosilane compositions are useful for a multitude of purposes. Such purposes include any known use for the preferred starting material organosilanes of the above-described general formula. In preferred embodiments, the presently described water-stabilized, organosilane compositions are suitable to applications such as: 1) treatment of surfaces, including fillers and pigments, 2) additives to coatings such as dyes, 3) additives to organic monomers (such as acrylics) prior to formation of the respective polymer, 4) addition to the polymer prior to processing into final products or 5) incorporation into polymer or substrate backbone, such as polyester or concrete.

Therefore, in addition to the utility of prior organosilane quaternary ammonium compounds, for example, 3-(trimethoxysilyl)propyl-dimethyloctadecyl ammonium chloride useful as surface bonding antimicrobial agents, numerous other uses of organofunctional silanes are contemplated, such as the diluted compositions of the invention in coating applications including the treatment of surfaces or particles (pigments or fillers), in primers, in paints, inks, dyes and adhesives, and as reactive intermediates for silicone resin synthesis.

The present invention can be used to prepare, inter alia, agricultural products, cleaning compositions, antimicrobial sponges, antimicrobial bleaching agents, antimicrobial fillers for paints, plastics, or concrete, and to treat concrete structures such as livestock shelters, where microbial infestation is a problem.

In various embodiment, surfaces and substrates treatable with the diluted compositions of the invention include, but are not limited to, textiles, carpet, carpet backing, upholstery, clothing, sponges, plastics, metals, surgical dressings, masonry, silica, sand, alumina, aluminum chlorohydrate, titanium dioxide, calcium carbonate, wood, glass beads, containers, tiles, floors, curtains, marine products, tents, backpacks, roofing, siding, fencing, trim, insulation, wall-board, trash receptacles, outdoor gear, water purification systems, and soil. Furthermore, articles treatable with the compositions of the invention include, but are not limited to, air filters and materials used for the manufacture thereof, aquarium filters, buffer pads, fiberfill for upholstery, fiberglass ductboard, underwear and outerwear apparel, polyurethane and polyethylene foam, sand bags, tarpaulins, sails, ropes, shoes, socks, towels, disposal wipes, hosiery and intimate apparel, cosmetics, lotions, creams, ointments, disinfectant sanitizers, wood preservatives, plastics, adhesives, paints, pulp, paper, cooling water, and laundry additives and non-food or food contacting surfaces in general.

For the above described substrates, mixtures and applications, treatment generally involves contacting or mixing the article to be treated with a water-stabilized organosilane composition, comprising the organosilane-stabilizer derived compound in an aqueous solution, for a period of time sufficient for permanent bonding of the active organosilane ingredient (or portion thereof) to the article. Generally, treatment begins almost immediately upon contact. Preferably, treatment requires from about 15 seconds to about 48 hours. More preferably, treatment requires from about 1 minute to about 24 hours. Even more preferably, treatment requires from about five minutes to 1 hour and most preferably, treatment requires about 30 minutes. Further general guidelines for application are as follows: For dipping a large object, it is preferred that about 1 to about 3 minutes of submersion is allowed in the solution, and then, the object is permitted to dry or is dried. However, some objects will benefit from very short dipping, mixing or contacting times. For example, fabric may pass through an aqueous bath of the composition at a rate of up to 40 yards per minute or more. After dipping, excess solution may be gently wiped or rinsed off. Alternatively, the solution may be sprayed on to the substrate. Moreover, the composition of the invention may be placed in a high intensity solid mixer and formed into a powder, which is then dried. The dried powder may then be used in a sprayer, if desired. In addition, the solutions may be wiped onto the substrate and applied using sponges or cloths, etc. Moreover, the solutions of the present invention can be added to pigments and fillers and stirred therewith for several (2-3) minutes. In addition, the solutions can be added to an emulsion or other existing formulation prior to use. Also, the solutions can be used in addition to, with, or as a spray coolant for extruded fibers. However, one of ordinary skill in the art would recognize that numerous other uses and modes of application are readily apparent from the stabilized organosilane compounds, products and compositions of the present invention and would, without undue experimentation, be able to determine effective application methods and treating times for any particular substrate, article, or other application. In addition, the compositions can be used in padding processes as are known in textile mills.

Moreover, after treating a surface or fabric with the compositions, the surface or fabric may, optionally, be heated to further complete bonding of the compound, product, or composition to the surface or substrate. Preferably, the surface or fabric is heated to a temperature of no more than 160° C. for several seconds.

The diluted water-stable organosilane compositions are, therefore, advantageous in treating a variety of substrates without the use of toxic organic solvents and provide for the safe, long-term storage of activated organosilanol compound that can be used without further preparation. Moreover, the stabilization scheme described herein does not interfere with the binding of the organosilane (or at least the core, operative portion thereof) to the substrate. In addition, the present invention provides a generally applicable scheme for solvating some water insoluble organosilanes.

Also apparent will be those applications where organosilanes $R_nSiX_{4-n}$ are prepared, dissolved, stored, applied, and in anyway used in water. Also apparent will be those applications of organosilanes $R_nSiX_{4-n}$ in other solvents or mixed in other media (solids, polymer mixes, fillers, pigments, powders, dyes or emulsions) where exposure to water occurs but could be detrimental due to undesired or untimely self-condensation of the silanol.

Moreover, the diluted organosilane compositions can be used in the incorporation of an organosilane antimicrobial agent in most textile goods (woven and non-woven) and yarns (synthetic and natural). The process provides articles that are durable, and the process itself is effective and does not require additional manufacturing steps or increased manufacturing cost.

Incorporating the compositions of the present invention during the dye process yields a textile material with a built-in antimicrobial agent with the organosilane characteristics, binding and antimicrobial protection. The incorporation process 1) does not add any additional step in the manufacturing process and does not require any equipment modification; and 2) is believed not to lose its antimicrobial characteristics and its effectiveness during further production of the textile goods. By incorporating the water-stable compositions of the present invention during the dye process, not only would the organosilane antimicrobial agent remain unaffected by the dying agent, but the end-product textile goods would also exhibit excellent dyeing properties.

The water-stabilized organosilane compositions are useful for a number of applications where the previous instability, insolubility prevented or, at least, hindered or restricted use of some organosilane agents. For example:

Treating food crops (for example, perishables such as vegetables, fruits, or grains) after removal (pickled/harvested) with the compositions imparts antimicrobial protection to the outer surface of the food crop. It is believed that such protection occurs without diffusing, migrating or leaching the antimicrobial agent from the bonded antimicrobial coating of the food item and provides prolonged, safe and non-toxic antimicrobial protection. The method involves treating fruits and vegetables in the rinse cycle, during or after the normal cleaning/water spraying, or during or after blanching. Thorough cleaning of fruits and vegetables at the processing plant is preferred for initially removing microorganisms. As one of ordinary skill in the art would recognize, machines are used initially to remove soil, chemicals used in growing, spoilage bacteria, and other foreign materials. These machines also use high velocity water sprays to clean the products. After the cleaning, raw foods or other crop materials are prepared for further processing such as blanching where the food is immersed in water at 190° F. to 210° F. or exposed to steam.

Microorganisms are controlled by the production plant up until the fruit or vegetable is removed. But once it is removed, organisms such as yeast, mold, and bacteria begin to multiply, causing the food to loose flavor and change in color and texture. To keep the food from spoiling, a number of methods have been employed, such as refrigerators, to slow down the microorganisms and delay deterioration. Unfortunately, such known methods will preserve raw foods for a few weeks at most. The compositions can preserve these items for extended periods. For instance, the compositions may be added to an existing water line feeding the sprayers for the foods, where such sprayers are used. Otherwise, a simple dipping process may be used, where the dipping requires only a few seconds to impart antimicrobial protection. Low concentrations of about 0.1 to about 1% aqueous solution (about 0.1 to about 1% by volume) of the compositions provide satisfactory results. In addition, it is believed that the presently described method can also control pathogens on poultry carcasses and in other susceptible meat and fish.

Treating baby milk/juice bottles, nipples, pacifiers and toys with the compositions of the present invention in the factory or leaching the agent from the bonded surface, can provide prolonged and safe/non-toxic antimicrobial protection. Treating such articles also eliminates odors caused by microbial contamination. A dipping method as described above may be used to treat these articles.

To date, parents have used soaps, detergents, and surface cleaners to alleviate the problems of contamination of these articles. However, these and other similar treatments have, for the most part, been inadequate and required repeated treatment. In addition, these treatments have been found to be limited in their ability to offer broad spectrum control of microorganisms. Therefore, the present compositions can be used to treat these articles to prevent microbial growth and contamination by coating an effective amount of the products and compounds of the invention thereon. The articles employed can be coated by allowing for about 1 to about 2 minutes submersion, for example, by dipping, and thereafter, the treated surface is allowed to dry at room temperature. The article is then rinsed of any excess antimicrobial agent. Thorough cleaning and sterilization is a preferred step in removing the microorganisms on the surface of the article prior to "coating" the article. In addition, preferably concentrations of about 10% or more by volume of the compositions of the invention are used for long lasting protection.

Treating surgical gloves with the compositions of the present invention before or during a surgical procedure can kill microorganisms on contact. It is believed that the treated gloves diffuse or leach the antimicrobial agent from the glove surface and provide prolonged antimicrobial activity with safe and non-toxic antimicrobial protection. Surgical gloves are treated, preferably, by submerging in the solution of the example, diluted to 1% W/V for at least 30 seconds. This method will permit doctors to use and, if necessary, re-use the same gloves (even without removing them) without undue fear of contamination.

Treating polymers and other materials such as concrete by incorporation into the bulk material protects from deterioration, odor build-up and potentially harmful contamination of the surface. Incorporation of a sun protection into polymers extends the life of the product.

Moreover, one of ordinary skill in the art would be able to implement numerous other end uses based upon the disclosure of the compounds, products and compositions of the present invention. Some uses require aqueous solutions, and some require non-aqueous environments. However, both applications are part of the invention. Furthermore, antimicrobial properties of the silane compounds according to the invention are only one of many possible properties. Mixtures of silanes according to the invention often provide additional benefits.

For instance, the following uses, applications and substrates, are contemplated:
1. Concrete, Concrete Water Conduits, Storm and Sewer-Pipes treated with the compounds, products and compositions of the present invention. Agents to kill microorganism on contact and provide prolonged antimicrobial protection to prevent deterioration of the concrete and its coatings.
2. Tooth Brushes, Combs, Hair Brushes, Dentures and Retainers
3. Spa and Pool Filters meeting stringent requirements that no other antimicrobial agent can meet and protection for Air Filtration such as air conditioning filters, HVAC applications and cabin air
4. Marble Slabs (building facia, tombs, floors) treated with the compounds, products and compositions of the present invention
5. Rubbing Alcohol
6. Statues and exposed art work
7. HDP (high density polyester) fabric plastic covers for dump sites, water reservoirs and generally for soil protection
8. Liquid Additive (as flower water preservative for potted plants and cut flowers)
9. Silicone and TEFLON coated Fiberglass with antimicrobial protection including acrylic backing wall covering
10. Dryvitt and Stucco finish
11. Waterproofing treated with the compounds, products and compositions of the present invention
12. A method of treating blended cotton before or after picking machines make the cotton into rolls or laps
13. Food packaging and containers
14. Bio-films and adhesives (tapes and silicone wafers)
15. Single Ply Roofing and Roof shingles
16. Fiberglass reinforcement product The invention will now be illustrated by the following Examples. In Example 1, the protocol for blending (reducing the concentration of organosilane) of the composition is described.

Example 1

Protocol for Production of Concentrated Compositions:
1. The ammonium chloride (QAC 80) is first added to water.
2. Next add Glycol Ether DB.
3. Mix well with a magnetic stir bar.
4. Add approximately 9 drops of 1 Molar HCL to 500 g (15%-25%), or approximately 2 drops of 1 Molar HCL to 100 g samples 30%-35% to adjust pH to 2.5 units while mixing.
5. Add the organosilane last and mix for 10 minutes (on warm heat for 20% and higher concentrates) until the mixture is uniform.

The concentrated solutions used in Tables 1 and 2 are made up as shown below:

|  | 10% active | | 15% active | | 20% active | |
|---|---|---|---|---|---|---|
|  | grams | % w/w | grams | % w/w | grams | % w/w |
| QAC 80 | 10.00 | 2.00% | 10.00 | 2.00% | 10.00 | 2.00% |
| 72% organosilane* | 69.35 | 13.87% | 104.02 | 20.80% | 138.70 | 27.74% |
| Glycol Ether DB | 100.00 | 20.00% | 100.00 | 20.00% | 100.00 | 20.00% |
| DI Water | 320.65 | 64.13% | 285.98 | 57.20% | 251.30 | 50.26% |
| Total | 500.00 | 100.00% | 500.00 | 100.00% | 500.00 | 100.00% |

|  | 25% active | | 30% active | | 35% active | |
|---|---|---|---|---|---|---|
|  | grams | % w/w | grams | % w/w | grams | % w/w |
| QAC 80 | 10.00 | 2.00% | 2.00 | 2.00% | 2.00 | 2.00% |
| 72% organosilane* | 173.37 | 34.67% | 41.61 | 41.61% | 48.54 | 48.54% |
| Glycol Ether DB | 100.00 | 20.00% | 20.00 | 20.00% | 20.00 | 20.00% |
| DI Water | 216.63 | 43.33% | 36.39 | 36.39% | 29.46 | 29.46% |
| Total | 500.00 | 100.00% | 100.00 | 100.00% | 100.00 | 100.00% |

*The organosilane is 3-(trihydroxysilyl) propyldimethyloctadecyl ammonium chloride (CAS #27668-52-6)

The stirring required for making up the concentrated compositions to be used in tables 1 and 2 is at least ten minutes with low heat as needed until a visually uniform mixture is achieved.

Example 2

The following results were observed when the organosilane compositions were diluted with water.

Table 1 shows the results of diluting active concentrate with DI water to make a lower % active diluted composition. The method is described below for each row in

TABLE 1

| % Active in Concentrated Composition | % Active in Diluted Composition | Comments |
| --- | --- | --- |
| 35 | 5 | solution immediately turns white with precipitate indicating polymerization |
| 30 | 5 | solution immediately turns white with precipitate indicating polymerization |
| 25 | 5 | solution immediately turns white with precipitate indicating polymerization |
| 20 | 5 | solution immediately turns white with precipitate indicating polymerization |
| 15 | 5 | solution immediately turns white with precipitate indicating polymerization |
| 10 | 5 | solution immediately turns white with precipitate indicating polymerization |
| 35 | 0.75 | solution stays clear and thin with no precipitate for 12-24 hours, then turns white with precipitate indicating polymerization |
| 30 | 0.75 | solution stays clear and thin with no precipitate for 12-24 hours, then turns white with precipitate indicating polymerization |
| 25 | 0.75 | solution stays clear and thin with no precipitate for 12-24 hours, then turns white with precipitate indicating polymerization |
| 20 | 0.75 | solution stays clear and thin with no precipitate for 12-24 hours, then turns white with precipitate indicating polymerization |
| 15 | 0.75 | solution stays clear and thin with no precipitate for 12-24 hours, then turns white with precipitate indicating polymerization |
| 10 | 0.75 | solution stays clear and thin with no precipitate for 12-24 hours, then turns white with precipitate indicating polymerization |

When a 1 ml of 35% active concentrated is diluted with 6 mls DI water to make a 5% active dilution the solution immediately turns white with precipitate indicating the polymerization has taken place.

When 1 ml of a 30% active concentrated is diluted with 5 mls DI water to make a 5% active dilution the solution immediately turns white with precipitate indicating the polymerization has taken place.

When 1 ml of a 25% active concentrated is diluted with 4 mls DI water to make a 5% active dilution the solution immediately turns white with precipitate indicating the polymerization has taken place.

When 1 ml of a 20% active concentrated is diluted with 3 mls DI water to make a 5% active dilution the solution immediately turns white with precipitate indicating the polymerization has taken place.

When 2 mls of a 15% active concentrated is diluted with 4 mls DI water to make a 5% active dilution the solution immediately turns white with precipitate indicating the polymerization has taken place.

When 2 mls of a 10% active concentrated is diluted with 2 mls DI water to make a 5% active dilution the solution immediately turns white with precipitate indicating the polymerization has taken place.

When 0.75 ml of a 35% active concentrated is diluted with 34.25 mls DI water to make a 0.75% active dilution the solution stays clear and thin with no precipitate for 12-24 hours, then turns white with precipitate indicating polymerization.

When 0.75 ml of a 30% active concentrated is diluted with 29.25 mls DI water to make a 0.75% active dilution the solution stays clear and thin with no precipitate for 12-24 hours, then turns white with precipitate indicating polymerization.

When 0.75 ml of a 25% active concentrated is diluted with 24.25 mls DI water to make a 0.75% active dilution the solution stays clear and thin with no precipitate for 12-24 hours, then turns white with precipitate indicating polymerization.

When 0.75 ml of a 20% active concentrated is diluted with 19.25 mls DI water to make a 0.75% active dilution the solution stays clear and thin with no precipitate for 12-24 hours, then turns white with precipitate indicating polymerization.

When 0.75 ml of a 15% active concentrated is diluted with 14.25 mls DI water to make a 0.75% active dilution the solution stays clear and thin with no precipitate for 12-24 hours, then turns white with precipitate indicating polymerization.

When 0.75 ml of a 10% active concentrated is diluted with 9.25 mls DI water to make a 0.75% active dilution the solution stays clear and thin with no precipitate for 12-24 hours, then turns white with precipitate indicating polymerization.

Example 3

In these experiments the organosilane compositions were diluted with 20% glycol ether. Table 2 shows the results of diluting active concentrated compositions with 20% Glycol Ether DB in DI water to obtain lower % active diluted compositions which show stability after 28 days. The method is described for each row in Table 2 below.

TABLE 2

| % Active in Concentrated Composition | % Active in Diluted Composition | Comments |
|---|---|---|
| 35 | 5 | solution is clear, thin, no precipitate indicating stability after 28 days |
| 30 | 5 | solution is clear, thin, no precipitate indicating stability after 28 days |
| 25 | 5 | solution is clear, thin, no precipitate indicating stability after 28 days |
| 20 | 5 | solution is clear, thin, no precipitate indicating stability after 28 days |
| 15 | 5 | solution is clear, thin, no precipitate indicating stability after 28 days |
| 10 | 5 | solution is clear, thin, no precipitate indicating stability after 28 days |
| 35 | 0.75 | solution is clear, thin, no precipitate indicating stability after 28 days |
| 30 | 0.75 | solution is clear, thin, no precipitate indicating stability after 28 days |
| 25 | 0.75 | solution is clear, thin, no precipitate indicating stability after 28 days |
| 20 | 0.75 | solution is clear, thin, no precipitate indicating stability after 28 days |
| 15 | 0.75 | solution is clear, thin, no precipitate indicating stability after 28 days |
| 10 | 0.75 | solution is clear, thin, no precipitate indicating stability after 28 days |

When 1 ml of 35% active concentrated is diluted with 6 mls of 20% Glycol Ether DB in DI water to make a 5% active dilution the solution is clear, thin, with no precipitate, indicating stability after 28 days.

When 1 ml of 30% active concentrated is diluted with 5 mls of 20% Glycol Ether DB in DI water to make a 5% active dilution the solution is clear, thin, with no precipitate, indicating stability after 28 days.

When 1 ml of 25% active concentrated is diluted with 4 mls of 20% Glycol Ether DB in DI water to make a 5% active dilution the solution is clear, thin, with no precipitate, indicating stability after 28 days.

When 1 ml of 20% active concentrated is diluted with 3 mls of 20% Glycol Ether DB in DI water to make a 5% active dilution the solution is clear, thin, with no precipitate, indicating stability after 28 days.

When 2 ml of 15% active concentrated is diluted with 4 mls of 20% Glycol Ether DB in DI water to make a 5% active dilution the solution is clear, thin, with no precipitate, indicating stability after 28 days.

When 2 ml of 10% active concentrated is diluted with 4 mls of 20% Glycol Ether DB in DI water to make a 5% active dilution the solution is clear, thin, with no precipitate, indicating stability after 28 days.

When 0.75 ml of a 35% active concentrated is diluted with 34.25 mls Glycol Ether DB in DI water to make a 0.75% active dilution the solution is clear, thin, with no precipitate, indicating stability after 28 days.

When 0.75 ml of a 30% active concentrated is diluted with 29.25 mls Glycol Ether DB in DI water to make a 0.75% active dilution the solution is clear, thin, with no precipitate, indicating stability after 28 days.

When 0.75 ml of a 25% active concentrated is diluted with 24.25 mls Glycol Ether DB in DI water to make a 0.75% active dilution the solution is clear, thin, with no precipitate, indicating stability after 28 days.

When 0.75 ml of a 20% active concentrated is diluted with 19.25 mls Glycol Ether DB in DI water to make a 0.75% active dilution the solution is clear, thin, with no precipitate, indicating stability after 28 days.

When 0.75 ml of a 15% active concentrated is diluted with 14.25 mls Glycol Ether DB in DI water to make a 0.75% active dilution the solution is clear, thin, with no precipitate, indicating stability after 28 days.

When 0.75 ml of a 10% active concentrated is diluted with 9.25 mls Glycol Ether DB in DI water to make a 0.75% active dilution the solution is clear, thin, with no precipitate, indicating stability after 28 days.

CONCLUSION

In conclusion, the solutions produced when the concentrated compositions are diluted with glycol ether are more stable than the solutions produced when the concentrated compositions are diluted with water.

The invention claimed is:

1. A method for reducing the concentration of organosilane in a first composition comprising an organosilane and an acidic stabilizing solution, wherein the acidic stabilizing solution comprises at least one acid, and at least one cationic surfactant in water, comprising adding glycol ether to the first composition to form a second, diluted composition.

2. The method according to claim 1 wherein the concentration of organosilane in the first composition is in the range 10 to 50% by weight of the composition.

3. The method according to claim 1 wherein the concentration of organosilane in the second diluted composition is in the range 0.001 to 15% by weight of the composition.

4. The method according to claim 1 wherein the first composition further comprises glycol ether.

5. The method according to claim 1, wherein the organosilane is of the formula $R_nSiX_{4-n}$, where n is an integer from 0 to 3, each R is, independently, a non-hydrolyzable organic group, and each X is, independently, a hydrolyzable group.

6. The method according to claim 5, wherein X is hydroxyl, alkoxy, acetoxy, unsubstituted or substituted acyl, or a halogen.

7. The method according to claim 1, wherein the organosilane is of the formula I, II, III, or IV

$$(R^1)_3SiR^2N^+(R^3)(R^4)(R^5)Y^- \tag{I}$$

$$(R^1)_3SiR^2N(R^3)(R^4) \tag{II}$$

$$(R^1)_3SiR^2R^{35} \tag{III}$$

$$(R^1)_2Si(R^{36})(R^{37}) \tag{IV}$$

wherein each $R^1$ is, independently, halogen or $R^6O$;

and wherein $R^6$ is H, alkyl from 1 to about 24 carbon atoms, acetyl, acetoxy, acyl, propylene glycol, ethylene glycol, polyethylene glycol, polypropylene glycol, block and copolymers of ethylene and propylene glycol, the alkyl monoether from 1 to 24 carbons of propylene glycol, ethylene glycol, polyethylene glycol, polypropylene glycol, block and copolymers of ethylene and propylene glycol, or the monoester of a carbonic acid from 1 to 24 carbons and propylene glycol, ethylene glycol, polyethylene glycol, polypropylene glycol, block and copolymers of ethylene and propylene glycol, octylphenol, nonylphenol, or sorbitan ethers;

and wherein $R^{35}$ is $R^6$, H, halogen, $NH_2(CH_2)_2NHR^2NH_2R^2$, $C_3H_5O_2R^2$, $C_4H_5O_2R^2$, $NaO(CH_3O)P(O)R^2$, or $ClCH_2C_6H_4R^2$;

and wherein $R^{36}$ and $R^{37}$ are, independently, $R^{35}$, halogen, H, alkyl, isobutyl, phenyl, or n-octyl;

and wherein $R^2$ is a divalent radical derived from benzyl, vinyl or alkyl from 1 to about 24 carbon atoms, acetyl, acetoxy, acyl, propylene glycol, ethylene glycol, polyethylene glycol, polypropylene glycol; block and copolymers of ethylene and propylene glycol, the alkyl monoether from 1 to 24 carbons of propylene glycol, ethylene glycol, polyethylene glycol, polypropylene glycol; block and copolymers of ethylene and propylene glycol or the monoester of a carbonic acid from 1 to 24 carbons and propylene glycol, ethylene glycol, polyethylene glycol, polypropylene glycol; block and copolymers of ethylene and propylene glycol; octylphenol, nonylphenol, or sorbitan ethers;

and wherein $R^3$ and $R^4$ are, independently, $R^{35}$, alkyl alcohol, alkoxy, or $R^3$ and $R^4$ can, together, form a morpholine or cyclic or heterocyclic, unsaturated or saturated, five- to seven-membered ring of the formula V:

(V)

where k is an integer from 0 to 2;

and wherein $R^7$, where the ring is saturated is $CH_2$, O, S, NH, $NH_2^+$, $NCH_2CH_2NH_2$, $NCH_2CH_2NH_3^+$, $NCH_2CH_2N(R^8)(R^9)$, $NCH_2CH_2N^+(R^8)(R^9)(R^{10})$, N(alkyl), N(aryl), N(benzyl), CH, N, $N^+H$, $N^+$(alkyl), $N^+$(aryl), $N^+$(benzyl), N—$CH_2$—N, $N^+H$—$CH_2$—N, $N^+$(alkyl)-$CH_2$—N, $N^+$(aryl)-$CH_2$—N, or $N^+$(benzyl)-$CH_2$—N;

and wherein each $R^8$, $R^9$, and $R^{10}$ is, independently, benzyl, $R^{37}$, polyether, alkyl alcohol, alkoxy, or alkyl;

and wherein $R^5$ is alkyl alcohol, $R^{35}$, $CH_2C_6H_5$, polyether, alkyl, perfluoroalkyl, perfluoroalkylsulfonate, perfluoroalkylcarboxylate, or is a five to seven-membered ring of formula V;

and wherein $Y^-$ is an anion.

8. The method according to claim 1, wherein the acidic stabilizing solution comprises exactly one acid, exactly one glycol ether, and exactly one cationic surfactant in water.

9. The method according to claim 1, wherein at least one acid is an inorganic acid.

10. The method according to claim 9, wherein the inorganic acid is a mineral acid.

11. The method according to claim 10, wherein the mineral acid is hydrochloric acid.

12. The method according to claim 1, wherein at least one acid is an organic acid.

13. The method according to claim 12, wherein the organic acid is acetic acid.

14. The method according to claim 1, wherein the glycol ether added to the first composition and/or the glycol ether in the acidic stabilizing solution is diethylene glycol butyl ether.

15. The method according to claim 1, wherein the at least one cationic surfactant is a quaternary ammonium salt.

16. The method according to claim 15, wherein the quaternary ammonium salt has the following structure:

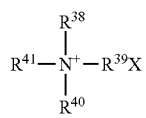

wherein each of $R^{38}$, $R^{39}$, $R^{40}$, and $R^{41}$ are independently selected from the group consisting of alkyl, aryl, and aralkyl, or the nitrogen may be part of a ring system; and wherein X is an anion.

17. The method according to claim 16, wherein at least one of $R^{38}$, $R^{39}$, $R^{40}$, or $R^{41}$ is an alkyl.

18. The method according to claim 15, wherein the quaternary ammonium salt is an N-alkyl-N,N-Dimethyl-N-Benzyl ammonium chloride.

19. The method according to claim 1, wherein the pH of the acidic stabilizing solution is between about 2 and about 3.

20. The method according to claim 19, wherein the pH of the acidic stabilizing solution is about 2.5.

21. The method according to claim 1, wherein the glycol ether added to the first composition and/or the glycol ether in the acidic stabilizing solution is not a polyol.

22. A method for producing a diluted antimicrobial organosilane composition, comprising:
a) mixing at least one cationic surfactant and optionally at least one glycol ether with water to produce a solution;
b) adding at least one acid to the solution to acidify the solution;
c) adding the solution to an organosilane to form an organosilane composition; and
d) adding glycol ether to the organosilane composition to produce the diluted anti-microbial organosilane composition.

23. The method according to claim 22 wherein step d) is carried out between one week and two years after the organosilane composition is formed.

24. The method according to claim 22 wherein step d) is carried out no more than 4 months after the organosilane composition is formed.

25. The method according to according to claim 22, comprising:
a) mixing exactly one quaternary ammonium salt with a glycol ether and water to produce a solution; and
b) adding exactly one acid to the solution to acidify the solution.

26. The method according to claim 22, wherein the pH of the solution after acidifying the solution is between about 2 and about 3.

27. The method according to claim 26, wherein the pH of the solution after acidifying the solution is about 2.5.

28. The method according to claim 22, wherein the at least one cationic surfactant is a quaternary ammonium salt which comprises about 0.1 wt % to about 5 wt % of the solution.

29. The method according to claim 22, wherein the at least one glycol ether comprises about 5 wt % to about 20 wt % of the solution.

30. The method according to claim 1 further comprising the step of treating a substrate with the diluted composition.

31. The method according to claim 30, wherein the substrate is coated with the composition and subsequently dried.

32. The method according to claim 30, comprising a further step of heating the substrate to bind the composition to the substrate.

33. The method according to claim 30, wherein the substrate is contacted with the composition for 15 seconds to 48 hours.

34. The method according to claim 30, wherein the composition further comprises at least one dye.

35. The method according to claim 30, wherein the substrate is selected from the group consisting of a concrete pipe, food article, fluid container, glove, latex medical article, a tooth brush, a comb, a hair brush, a denture, an orthodontic retainer, a spa or pool filter, an air filter, an HVAC air system, a cabin air system, a marble article, a statue, an exposed work of art, an HDP plastic cover, a silicone or TEFLON® coated fiberglass article, a Dryvitt™ finish, a stucco finish, blended cotton, a bio-film, a bio-adhesive, a single ply roofing, a roofing shingle, and a fiberglass reinforcement product, a textile, a carpet, a carpet backing, a clothing article, a sponge, a plastic, a metal, a surgical dressing, masonry, sand, silica, alumina, alumina chlorohydrate, titanium dioxide, calcium carbonate, wood, a glass bead, a tile, a floor, a curtain, a marine product, a tent, a backpack, roofing, siding, fencing, trim, insulation, wall-board, a trash receptacle, a water purification system, soil, a buffer pad, an aquarium filter, a sand bag, a sail, a rope, a tarpaulin, a shoe, a sock, a towel, a disposable wipe, and hosiery.

36. The method according to claim 30, wherein the substrate is antimicrobially enhanced.

37. The method according to claim 1 further comprising a step of antimicrobially enhancing a product, comprising admixing the product with the diluted composition.

38. The method according to claim 37, wherein the diluted composition is admixed with a product selected from the group consisting of polyester, concrete, a primer, a paint, an ink, a dye, an adhesive, an agricultural product, a plastic, a bleaching agent, a cosmetic, a lotion, a cream, an ointment, a disinfectant sanitizer, a wood preservative, pulp, paper, cooling water, a laundry additive, rubbing alcohol, a flower preservative, and a waterproofing solution.

39. The method according to claim 37, wherein the composition further comprises at least one dye.

* * * * *